US012365650B2

(12) United States Patent
Vadodaria et al.

(10) Patent No.: US 12,365,650 B2
(45) Date of Patent: Jul. 22, 2025

(54) DEUTERATED ORGANIC COMPOUNDS AND USES THEREOF

(71) Applicant: ENGRAIL THERAPEUTICS, INC., San Diego, CA (US)

(72) Inventors: Krishna Vadodaria, San Diego, CA (US); Kimberly Vanover, Tulsa, OK (US); Vikram Sudarsan, San Diego, CA (US); David Garvey, Dover, MA (US)

(73) Assignee: ENGRAIL THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/761,559

(22) Filed: Jul. 2, 2024

(65) Prior Publication Data

US 2025/0011279 A1 Jan. 9, 2025

Related U.S. Application Data

(60) Provisional application No. 63/511,685, filed on Jul. 2, 2023, provisional application No. 63/511,847, filed on Jul. 3, 2023, provisional application No. 63/511,849, filed on Jul. 3, 2023, provisional application No. 63/511,852, filed on Jul. 3, 2023, provisional application No. 63/511,853, filed on Jul. 3, 2023, provisional application No. 63/511,855, filed on Jul. 3, 2023, provisional application No. 63/512,064, filed on Jul. 5, 2023.

(51) Int. Cl.
| | |
|---|---|
| C07D 207/14 | (2006.01) |
| A61K 31/40 | (2006.01) |
| A61K 31/402 | (2006.01) |
| A61P 25/22 | (2006.01) |
| A61P 25/24 | (2006.01) |
| C07B 59/00 | (2006.01) |
| C07D 207/09 | (2006.01) |

(52) U.S. Cl.
CPC ............ *C07D 207/14* (2013.01); *A61K 31/40* (2013.01); *A61K 31/402* (2013.01); *A61P 25/22* (2018.01); *A61P 25/24* (2018.01); *C07B 59/004* (2013.01); *C07D 207/09* (2013.01); *C07B 2200/05* (2013.01)

(58) Field of Classification Search
CPC ........ C07D 207/14; A61P 25/24; A61K 31/40
See application file for complete search history.

(56) References Cited

U.S. PATENT DOCUMENTS

| | | | |
|---|---|---|---|
| 4,197,243 | A | 4/1980 | Murakami et al. |
| 4,210,660 | A | 7/1980 | Takashima et al. |
| 5,624,687 | A | 4/1997 | Yano et al. |
| 6,436,441 | B1 | 8/2002 | Sako et al. |
| 6,872,405 | B2 | 3/2005 | Takaishi et al. |
| 2019/0328745 | A1 | 10/2019 | Vanover et al. |
| 2019/0343827 | A1 | 11/2019 | Bunt |
| 2021/0017160 | A1 | 1/2021 | Lee et al. |

FOREIGN PATENT DOCUMENTS

| | | |
|---|---|---|
| CN | 104744333 A | 7/2015 |
| WO | WO 94/10174 A1 | 5/1994 |
| WO | WO 2020/176597 A1 | 9/2020 |
| WO | WO 2023/130117 A1 | 7/2023 |
| WO | WO 2023/130119 A1 | 7/2023 |
| WO | WO 2025/010255 A2 | 1/2025 |
| WO | WO 2025/010259 A2 | 1/2025 |

OTHER PUBLICATIONS

Hoang (Year: 2008).*
Higuchi (Year: 1986).*
Tung (Year: 2010).*
Marseille et al (Year: 2020).*
CAS RN3067217-43-7 (Year: 2025).*
U.S. Appl. No. 18/726,550, filed Jul. 3, 2024, Vadodaria et al.
U.S. Appl. No. 18/763,819, filed Jul. 3, 2024, Vadodaria et al.
Admon, R. et al., "Dopaminergic enhancement of striatal response to reward in major depression," HHS Public Access, Author manuscript, available in PMC 2018, 16 pages, face of article states: Published in final edited form as: Am J Psychiatry. 2017; 174(4): 378-386, doi:10.1176/appi.ajp.2016.16010111.
Bishara, D. et al., "Upcoming Agents for the Treatment of Schizophrenia," Drugs, 2008, 68 (16), 2269-2292.
Celada, P. et al., "Serotonin 5-HT1A Receptors as Targets for Agents to Treat Psychiatric Disorders: Rationale and Current Status of Research," CNS Drugs, 2013, 27, 703-716.
CN 104744333 A published Jul. 1, 2015, and English machine translation thereof (on last page), 4 pages total.
Curran, M. et al., "Amisulpride," Drugs, 2001, 61 (14), 2123-2150.
Di Martino, R. et al., "Deuterium in drug discovery: progress, opportunities and challenges," Nature Reviews Drug Discovery, 2023, 22, 562-584.
Dyck, L. et al., "Effects of Deuterium Substitution on the Catabolism of β-Phenylethylamine: An In Vivo Study," Journal of Neurochemistry, 1986, 46 (2), 399-404.
English translation (20 pages) of Nakayama, K. et al., "Examination of clinical usability of nemonapride on postpsychotic depression," Clinical Psychiatry, 1995, 24 (5), 595-604.
Ford, C., "The Role of D2-Autoreceptors in Regulating Dopamine Neuron Activity and Transmission," HHS Public Access, Author manuscript, available in PMC 2015, 21 pages, face of article states: Published in final edited form as: Neuroscience. 2014, 282: 13-22, doi: 10.1016/j.neuroscience.2014.01.025.

(Continued)

*Primary Examiner* — Jeffrey S Lundgren
*Assistant Examiner* — Ibrahim D Bori
(74) *Attorney, Agent, or Firm* — Hoxie & Associates LLC

(57) ABSTRACT

Provided are compounds of Formula I and Formula II, described herein, processes for their preparation, their use as pharmaceuticals, and pharmaceutical compositions comprising them and intermediates used in their preparation. Compounds of Formula I and Formula II are useful, for instance, in modulating dopamine and serotonin neurotransmission and treating disorders that may benefit from the same, such as schizophrenia and depression.

26 Claims, 8 Drawing Sheets

(56) References Cited

OTHER PUBLICATIONS

Furrow, M. et al., "Protecting deuterated drugs," Intellectual Property Magazine, dated 2018, 35-36, retrieved on Jan. 3, 2025, from: https://www.venable.com/-/media/files/publications/2018/02/protecting-deuterated-drugs.pdf?rev=e1b96c24e5ea433c89765760321b71ad&hash=9CF3EC763FA6B87D49C9125B BD18F522.

Garcia-Garcia, A. et al., "5-$HT_{1A}$ receptors in mood and anxiety: recent insights into autoreceptor versus heteroreceptor function," NIH Public Access, Author manuscript, available in PMC 2015, 24 pages, face of article states: Published in final edited form as: *Pyschopharmacology (Berl).* 2014, 231(4): 623-636, doi:10.1007/s00213-013-3389-x.

Harbeson, S. et al., "Deuterium Medicinal Chemistry: A New Approach to Drug Discovery and Development," Medchem News, 2014, No. 2, 8-22.

Hatano, K. et al., "Synthesis of ω-[$^{18}$F]Flouroalkyl Analogs of YM-09151-2 for the Measurement of $D_2$-Dopamine Receptors with PET," Applied Radiation and Isotopes, 1990, 41 (6), 551-555.

Hernandes, M. et al., "Halogen Atoms in the Modern Medicinal Chemistry: Hints for the Drug Design," Current Drug Targets, 2010, 11, 12 pages.

Iwanami, S. et al., "Synthesis and Neuroleptic Activity of Benzamides, cis-N-(1-Benzyl-2-methylpyrrolidin-3-y1)-5-chloro-2-methoxy-4-(methylamino)benzamide and Related Compounds," Journal of Medicinal Chemistry, 1981, 24, 1224-1230.

Kurczab, R. et al., "The Significance of Halogen Bonding in Ligand-Receptor Interactions: The Lesson Learned from Molecular Dynamic Simulations of the $D_4$ Receptor," Molecules, 2020, 25, 91, doi:10.3390/molecules25010091, 14 pages.

Kusumi, I. et al., "Psychopharmacology of atypical antipsychotic drugs: From the receptor binding profile to neuroprotection and neurogenesis," Psychiatry and Clinical Neurosciences, 2015, 69, 243-258.

Lavergne, F. et al., "A new strategy for antidepressant prescription," Frontiers in Neuroscience, 2010, 4, Article 192, 13 pages, doi: 10.3389/fnins.2010.00192.

Li, P. et al., "Dopamine Targeting Drugs for the Treatment of Schizophrenia: Past, Present and Future," Current Topics in Medicinal Chemistry, 2016, 16, 3385-3403.

Ly, C. et al., "Psychedelics Promote Structural and Functional Neural Plasticity," Cell Reports, 2018, 23, 3170-3182.

Mckeage, K. et al., "Amisulpride," CNS Drugs, 2004, 18 (13), 933-956.

Mishra, A. et al., "Physiological and Functional Basis of Dopamine Receptors and Their Role in Neurogenesis: Possible Implication for Parkinson's disease," Journal of Experimental Neuroscience, 2018, 12, 8 pages, doi: 10.1177/1179069518779829.

Nakayama, K. et al., "Examination of clinical usability of nemonapride on postpsychotic depression," Clinical Psychiatry, 1995, 24 (5), 595-604.

NeuroPerspective, "Psychedelics, Epilepsy, Rett Syndrome," dated Summer (Jul.-Sep.) 2022, No. 319-321, ISSN 1537-6346, pp. 3-39 and 66.

Newman-Tancredi, A., "Novel antipsychotics activate recombinant human and native rat serotonin 5-HT1A receptors: affinity, efficacy and potential implications for treatment of schizophrenia," International Journal of Neuropsychopharmacology, 2005, 8, 341-356.

Newman-Tancredi, A., "Biased agonism at serotonin 5-$HT_{1A}$ receptors: preferential postsynaptic activity for improved therapy of CNS disorders," Neuropsychiatry, 2011, 1 (2), 149-164.

Noda-Saita, K. et al., "Dopamine D4-like Binding Sites Labeled by [$^3$H]Nemonapride Include Substantial Serotonin 5-HT2A Receptors in Primate Cerebral Cortex," Biochemical and Biophysical Research Communications, 1999, 255, 367-370.

Pubchem CID 4452, Modify date listed as: Feb. 24, 2023, 2 pages, retrieved by USPTO as ISA in International Application No. PCT/US2023/010055 on Mar. 3, 2023, from: https://pubchem.ncbi.nlm.nih.gov/compound/4452.

Pubchem SID 85789047, Modify date listed as: Mar. 8, 2010, 8 pages, retrieved by USPTO as ISA in International Application No. PCT/US2023/010050 on Feb. 27, 2023, from: https://pubchem.ncbi.nlm.nih.gov/substance/85789047.

Rao, N. et al., "Deuterated Drugs," Pharmaceutical Chemistry Journal, 2022, 55 (12), 1372-1377.

Schotte, A. et al., "In Vitro Receptor Binding and In Vivo Receptor Occupancy in Rat and Guinea Pig Brain: Risperidone Compared with Antipsychotics Hitherto Used," Japanese Journal of Pharmacology, 1995, 69, 399-412.

Seeman, P. et al., "Deriving the therapeutic concentrations for clozapine and haloperidol: The apparent dissociation constant of a neuroleptic at the dopamine $D_2$ or $D_4$ receptor varies with the affinity of the competing radioligand," European Journal of Pharmacology, 1995, 291, 59-66.

Tamazawa, K. et al., "Synthesis of [Carbonyl-$^{14}$C]- and (Methoxy-$d_3$)-labeled N-[(2RS,3RS)-1-Benzyl-2-methyl-3-pyrrolidinyl]-5-chloro-2-methoxy-4-(methylamino) Benzamide (YM-09151-2), A New Potent Neuroleptic Agent," Journal of Labelled Compounds and Radiopharmaceuticals, 1984, XXI (5), 441-453.

Wang, P. et al., "Use of antipsychotics in the treatment of depressive disorders," Shanghai Archives of Psychiatry, 2013, 25 (3), 134-140.

Wang, X-M. et al., "Effect of deuteration on the single dose pharmacokinetic properties and postoperative analgesic activity of methadone," HHS Public Access, Author manuscript, available in PMC 2023, 26 pages, face of article states: Published in final edited form as: *Drug Metab Pharmacokinet.* 2022; 47: 100477, doi:10.1016/j.dmpk.2022.100477.

Zhang, G. et al., "The role of serotonin 5-HT2A receptors in memory and cognition," Frontiers in Pharmacology, 2015, 6, Article 225, 17 pages, doi: 10.3389/fphar.2015.00225.

\* cited by examiner

DEUTERATED ORGANIC COMPOUNDS AND USES THEREOF

This application claims priority to U.S. Provisional Application No. 63/511,685 filed Jul. 2, 2023, U.S. Provisional Application No. 63/511,847 filed Jul. 3, 2023, U.S. Provisional Application No. 63/511,849 filed Jul. 3, 2023, U.S. Provisional Application No. 63/511,852 filed Jul. 3, 2023, U.S. Provisional Application No. 63/511,853 filed Jul. 3, 2023, U.S. Provisional Application No. 63/511,855 filed Jul. 3, 2023, and U.S. Provisional Application No. 63/512,064 filed Jul. 5, 2023, the contents of each of which are hereby incorporated by reference in their entireties.

FIELD

Provided are compounds of Formula I and Formula II, described below, processes for their preparation, their use as pharmaceuticals, and pharmaceutical compositions comprising them and intermediates used in their preparation. Compounds of Formula I and Formula II are useful, for instance, in modulating dopamine and serotonin neurotransmission and treating disorders that may benefit from the same, such as schizophrenia and depression.

BACKGROUND

Dopamine is involved in a variety of central nervous system functions, including voluntary movement, feeding, affect, reward, sleep, attention, working memory, and learning. Serotonin also is involved in a variety of central nervous system functions, including mood, cognition, reward, learning, memory, and various physiological processes. Accordingly, dopaminergic and/or serotonergic dysfunction can lead to diseases such as schizophrenia and depression.

When released from presynaptic terminals, dopamine activates members of a family of G protein-coupled dopamine receptors D1-D5. Dopamine receptors (D1-D5) are divided into two groups, the D1-like (D1 and D5) and the D2-like (D2, D3, and D4). Activation of D1-like receptors activates adenylyl cyclase and increases cAMP levels. D2-like receptors are inhibitory. Activation of D2-like receptors inhibits activation of adenylyl cyclase.

D1-like receptors are found postsynaptically on dopamine-receptive cells, while D2-like dopamine receptors are expressed both postsynaptically on dopamine target cells and presynaptically on dopaminergic neurons.

Fourteen serotonin receptor subtypes, grouped into subfamilies, mediate effects of serotonin (5-HT). The 5-HT1A receptor subtype, a major receptor subtype, exists as presynaptic autoreceptor in serotonin neurons in the raphe nuclei and as postsynaptic heteroreceptors in the prefrontal cortex, hippocampus, septum, and hypothalamus. Signaling mechanisms of 5-HT1A receptors in the raphe nuclei may be different from 5-HT1A receptors in other brain regions. Activation of 5-HT1A postsynaptic receptors can elicit increased dopamine release. The 5-HT2A receptor subtype is enriched in cortex and is linked to phosphatidylinositol turnover and also modulates dopamine release. 5-HT2A receptor antagonists have antipsychotic properties, while 5-HT2A receptor agonism is thought to be associated with cognition-enhancing and hallucinogenic properties. The hallucinogenic effects of lysergic diethylamide (LSD) and psilocybin are thought to arise from their 5-HT2A receptor agonism. 5-HT2A agonism has also been reported to promote neural plasticity and reduce depression.

Antipsychotics are used to manage psychosis, in particular schizophrenia. A hallmark of antipsychotics is D2 receptor antagonism. D2 receptor antagonism is effective in reducing positive symptoms of schizophrenia (for instance, hallucinations and delusions), but often also produces extrapyramidal side effects, including parkinsonism, akathisia, and tardive dyskinesia, increases prolactin, and may exacerbate negative symptoms of schizophrenia (for instance, loss of interest and motivation in life and activities, social withdrawal, and anhedonia). A key feature of atypical antipsychotics is D2 receptor antagonism in combination with 5-HT2A receptor antagonism, which may explain their enhanced efficacy and reduced extrapyramidal motor side effects (EPS) compared to typical antipsychotics. Many psychotic patients also suffer from depression, which may be left untreated by current medications. However, some atypical antipsychotics are used adjunctively to serotonergic antidepressants to improve response in major depressive disorder.

Because imbalances in dopamine and serotonin can lead to a variety of disorders and current medications may not be able to effectively modulate levels of both, new compounds that can modulate dopamine and serotonin neurotransmission are needed, as are methods of treating diseases that involve imbalances in dopamine and serotonin.

BRIEF SUMMARY

Provided is a compound of Formula I:

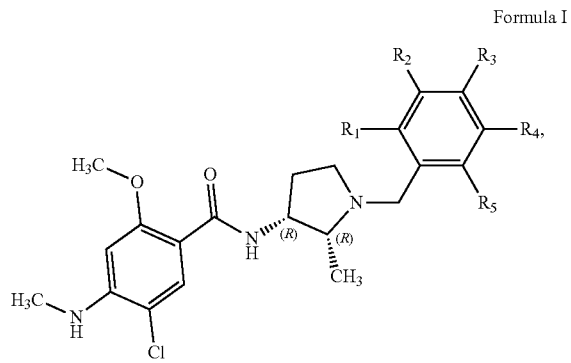

Formula I wherein:
$R_1$, $R_2$, $R_3$, $R_4$, and $R_5$ are independently selected from H and D; and
at least one of $R_1$, $R_2$, $R_3$, $R_4$, and $R_5$ is D;
in free or salt form.

Further provided are pharmaceutical compositions comprising compounds of Formula I, processes for preparing compounds of Formula I, and pharmaceutical uses of compounds of Formula I, for instance, as an anti-anhedonic agent and to treat schizophrenia, depression, and post-traumatic stress disorder.

Provided is a compound of Formula II:

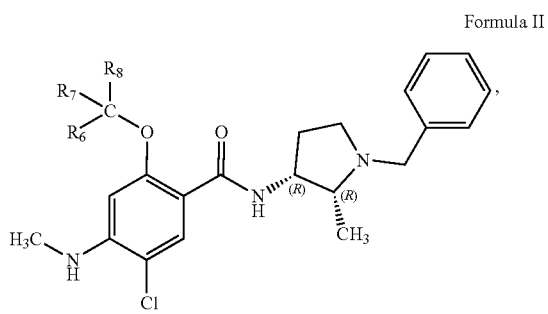

Formula II wherein:
$R_6$, $R_7$, and $R_8$ are independently selected from H and D; and
at least one of $R_6$, $R_7$, and $R_8$ is D;
in free or salt form,
wherein the compound is substantially free of its (S,S) enantiomer.

Further provided are pharmaceutical compositions comprising compounds of Formula II, processes for preparing compounds of Formula II, and pharmaceutical uses of compounds of Formula II, for instance, as an anti-anhedonic agent and to treat schizophrenia, depression, and post-traumatic stress disorder.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

DETAILED DESCRIPTION

Figure 1:
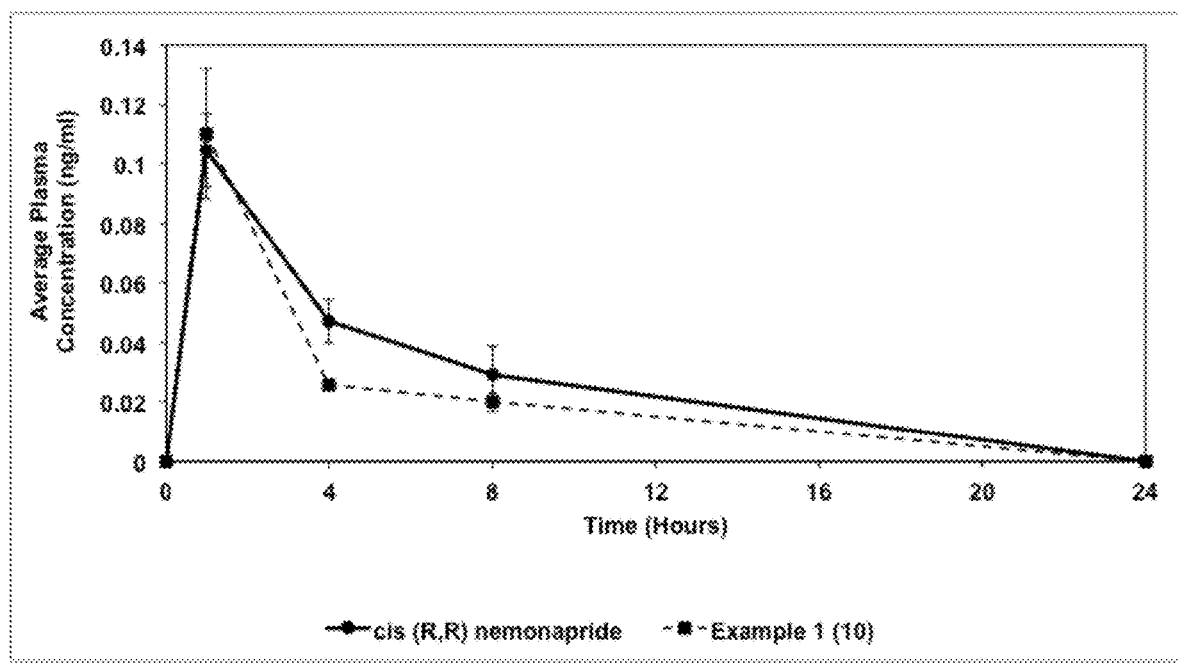
FIG. 1 shows average plasma concentration (ng/ml) in rats of cis (R,R) nemonapride and the compound of Example 1 (10) when administered at a single PO dose of 0.5 mg/kg.

The following description of the preferred embodiment(s) is merely exemplary in nature and is in no way intended to limit the invention, its application, or uses.

In the event of a conflict in a definition in the present disclosure and that of a cited reference, the present disclosure controls.

D2- and D3-receptors are expressed both postsynaptically on dopamine target cells and presynaptically on dopamine neurons. Dopamine receptors are mainly located on non-dopamine neurons. Dopamine receptors on dopamine neurons are called autoreceptors. Autoreceptors contribute to regulating dopamine neuron activity and controlling the synthesis, release, and uptake of dopamine.

Presynaptic D2-like dopamine autoreceptors regulate dopamine release. A low dose of a D2-like receptor antagonist may preferentially block presynaptic autoreceptors and increase dopamine release, while a high dose may block postsynaptic receptors and decrease dopamine neurotransmission. Relatively high occupancy of D2-like receptors has been associated with antipsychotic effects, while lower occupancy has been associated with antidepressant effects.

Anhedonia is a core symptom of major depressive disorder (MDD) and is associated with inadequate response to approved selective serotonin reuptake inhibitors (SSRIs) and serotonin norepinephrine reuptake inhibitors (SNRIs) and psychotherapy (e.g., cognitive behavioral therapy (CBT)) and neurostimulation (e.g., transcranial magnetic stimulation (TMS)). There remains a need for effective treatment of MDD characterized by anhedonia. Despite a range of available therapies, up to 50% of people suffering from MDD fail to respond to treatments, and only about 30% of patients fully recover after receiving currently available antidepressants and treatment outcomes are even poorer for MDD individuals with anhedonia.

Depletion of dopamine/catecholamines induces symptoms of depression and anhedonia. Increasing dopamine neurotransmission can alleviate symptoms of depression and anhedonia. However, while a high dose of a dopamine D2/D3 agonist may activate dopamine post-synaptic receptors, it can also be poorly tolerated (e.g., nausea/vomiting). Low dose of a dopamine D2/D3 receptor antagonist may preferentially block pre-synaptic dopamine autoreceptors and increase dopamine release without being poorly tolerated.

Besides MDD, anhedonia also plays a role in bipolar disorder, schizophrenia, post-traumatic stress disorder, and substance use disorder. Despite its role in many disorders, there are no approved medications to treat anhedonia.

Decreased serotonergic activity has been implicated in anxiety and depression. Increasing serotonin neurotransmission may alleviate symptoms of anxiety and depression and be helpful for anxious depression.

The IUPAC name of nemonapride is (±)-cis-N-(1-Benzyl-2-methylpyrrolidin-3-yl)-5-chloro-2-methoxy-4-methyl-aminobenzamide. Nemonapride is described in U.S. Pat. No. 4,210,660 as a strong central nervous system depressant, in particular a strong antipsychotic.

Nemonapride is a dopamine D2/D3/D4 receptor antagonist. Nemonapride is approved in Japan and South Korea for treatment of schizophrenia. Nemonapride is supplied as 3 mg and 10 mg tablets. The approved daily dose of nemonapride for schizophrenia is 9 to 36 mg given orally in divided doses after meals. The dose can be increased up to 60 mg daily.

The nemonapride prescribing information indicates that the elimination half-life when nemonapride 3 mg and 6 mg was administered orally to healthy adults was 2.3 to 4.5 hours. Urinary metabolites of nemonapride result from debenzylation and N-demethylation. See Emilace package insert.

In addition to being a dopamine D2/D3/D4 receptor antagonist, nemonapride is also a 5-HT1A agonist. Further, nemonapride has been reported to bind to 5-HT2A receptors, however, the inventors are not aware of any publication that reports its functional effect at that receptor. Yet, as an antipsychotic, it may be expected that nemonapride is a 5-HT2A receptor antagonist because a key feature of atypical antipsychotics is D2 receptor antagonism in combination with 5-HT2A receptor antagonism or inverse agonism.

When a drug is used as a mixture of stereoisomers, it is not possible to predict what properties (e.g., biological target, pharmacokinetics) each stereoisomer has, especially a drug that has multiple biological targets.

Compounds of Formula I and Formula II disclosed herein are D2 receptor antagonists and 5-HT2A agonists. Surprisingly, the deuterated compounds of Example 1 and Example 2 show higher 5-HT2A agonism than their non-deuterated analog (see Example 4, Table 5). The deuterated compound of Example 1 (10) is also a 5-HT1A agonist and the deuterated compound of Example 2 (18) is also a 5-HT1A partial agonist. D2 receptor antagonism in combination with 5-HT1A and 5-HT2A agonism, in particular strong 5-HT2A agonism, is a unique pharmacological activity profile, which may allow for differential modulation of dopamine and serotonin neurotransmission compared to other D2 receptor antagonists. Other substituted benzamides tested—R-remoxipride, S-remoxipride, R-sulpiride, R-sulfopride, and S-sulfopride—do not even bind to the 5-HT2A receptor in vitro (labeled-Ketansrin competition assay).

As noted above, D2 receptor antagonism in combination with 5-HT1A and 5-HT2A agonism is a unique activity profile, which may allow for different modulation of dopamine and serotonin neurotransmission compared to other D2 receptor antagonists. For instance, D2 postsynaptic receptor antagonism reduces psychosis, particularly in schizophrenia, by reducing dopamine neurotransmission. High doses that target ≥60% receptor occupancy may be associated with D2 antagonist mediated side effects such as extrapyramidal motor side effects (EPS) and increased prolactin. However, 5-HT1A agonism may limit those high dose D2 antagonist related side effects, thus providing the compounds with a built-in safety feature when used at high dose as an antipsychotic. 5-HT1A agonism also provides anxiolytic effects. Further, as strong 5-HT2A agonists, deuterated compounds disclosed herein may show enhanced antidepressant effects as seen with psychedelic antidepressants, for instance, rapid and long-lasting and with anxiolytic effects. And, D2 antagonism in combination with 5-HT2A agonism may modulate 5-HT2A hallucinogenic effects.

Thus, as D2 antagonists and 5-HT2A agonists, compounds of Formula I and Formula II may provide psychedelic-like antidepressant efficacy at low doses (e.g., doses lower than those of nemonapride used to treat schizophrenia), but also have built-in protection against 5-HT2A mediated hallucinations. Further, as D2 antagonists and 5-HT1A agonists, compounds of Formula I and Formula II may act as antipsychotics at high doses, but have built-in protection against high dose D2 antagonist related side effects.

Surprisingly, different deuteration patterns of N-[(2R,3R)-1-benzyl-2-methylpyrrolidin-3-yl]-5-chloro-2-methoxy-4-(methylamino)benzamide result in distinct activity profiles, particularly with respect to 5-HT2A agonism relative to D2 antagonism. Data indicates that the deuterated compounds of Example 1 (10) and Example 2 (18) disclosed herein show weaker D2L antagonism and stronger 5-HT2A agonism compared to their non-deuterated analog. In addition, data indicates that the compounds of Example 1 (10) and Example 2 (18) herein are also stronger 5-HT2A agonists than the compound of Example 1 (A2) in International Publication No. WO 2023/130117. The differences result in a more balanced 5HT2A:D2L ratio (see Table 6) for the compounds of Example 1 (10) and Example 2 (18). The distinct activity profiles of these compounds to two targets (dopamine and serotonin receptors) may allow the compounds to be targeted to and particularly beneficial in different patient populations.

Figure 2:
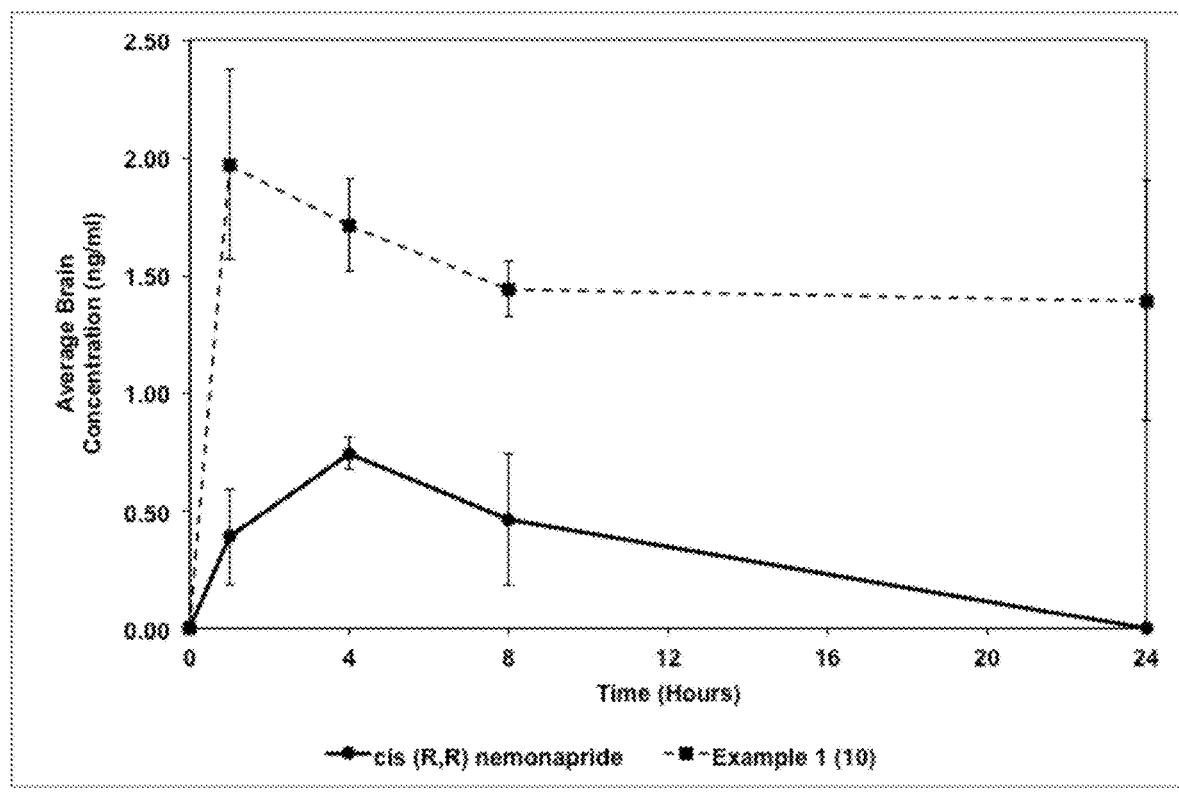
FIG. 2 shows average brain concentration (ng/ml) in rats of cis (R,R) nemonapride and the compound of Example 1 (10) when administered at a single PO dose of 0.5 mg/kg.
Figure 4:
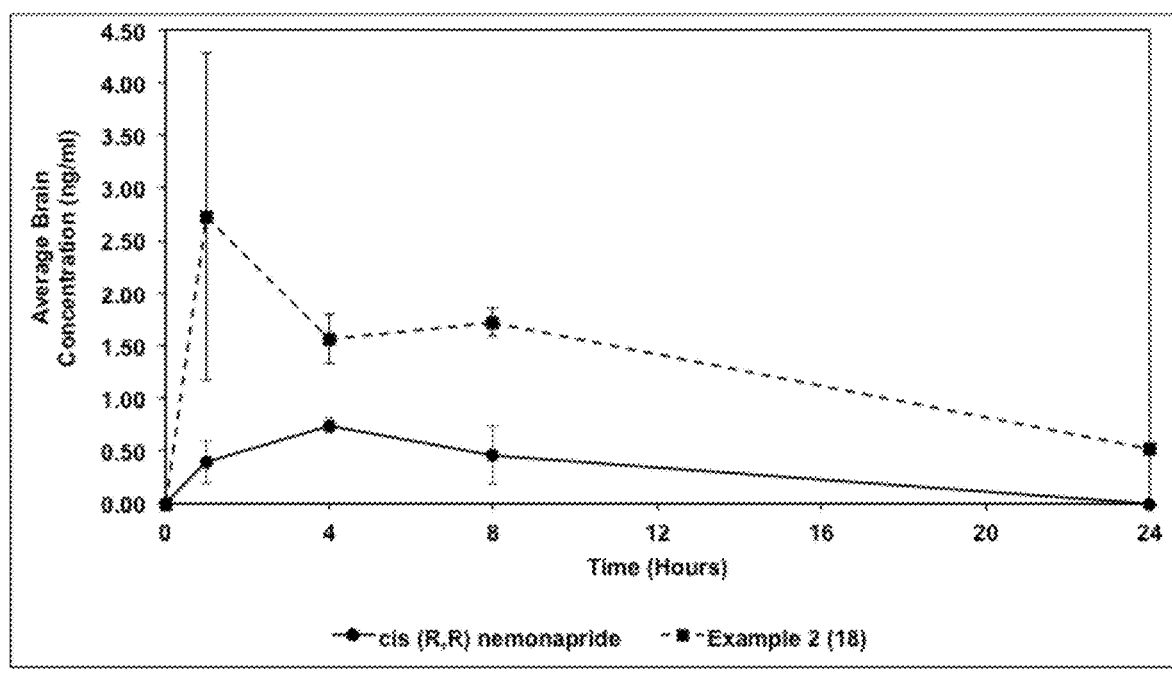
FIG. 4 shows average brain concentration (ng/ml) in rats of cis (R,R) nemonapride and the compound of Example 2 (18) when administered at a single PO dose of 0.5 mg/kg.

Pharmacokinetics of deuterated compounds disclosed herein are beneficial. Plasma pharmacokinetics of N-[(2R, 3R)-1-benzyl-2-methylpyrrolidin-3-yl]-5-chloro-2-methoxy-4-(methylamino)benzamide (cis (R,R) nemonapride) and the deuterated compounds of Example 1 (10) and Example 2 (18) are similar (see Example 5). However, despite similar plasma pharmacokinetics, Example 5 shows that compounds of Formula I and Formula II (deuterated compounds of Example 1 (10) and Example 2 (18)) have enriched and retained brain levels compared to their non-deuterated analog. For instance, FIGS. 2 and 4 show higher brain levels at all time points of the compounds of Example 1 (10) and Example 2 (18) compared to cis (R,R) nemonapride. The deuterated compounds of Example 1 (10) and Example 2 (18) also show extended brain enrichment compared to plasma levels of the compound (see FIGS. 5 and 6). The brain:plasma exposure supports once-daily dosing of both. Enriched brain levels and extended brain enrichment compared to plasma levels are beneficial features that allows for higher and more sustained receptor occupancy with less frequent dosing and may be associated with fewer peripheral side effects. Receptor occupancy levels provided by the deuterated compounds of Example 1 (10) and Example 2 (18) may be maintained in a desired range with a convenient dosing regime. In contrast, nemonapride is taken in multiple doses per day.

Compounds that are D2 receptor antagonists, 5-HT1A receptor agonists, and 5-HT2A receptor agonists modulate dopamine and serotonin neurotransmission and are therefore useful in treating disorders involving dopamine and serotonin signaling pathways, for instance, disorders involving dopamine, 5-HT1A, and/or 5-HT2A receptors.

Provided is a compound of Formula I:

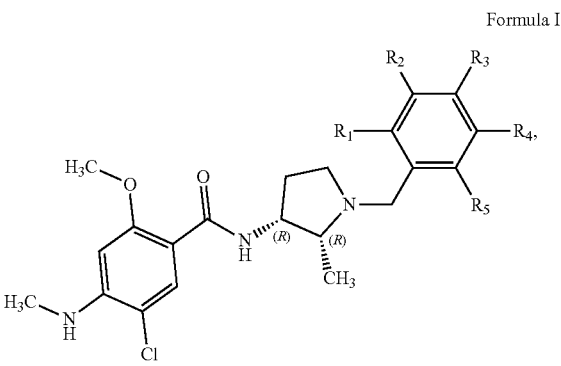

Formula I wherein:

$R_1$, $R_2$, $R_3$, $R_4$, and $R_5$ are independently selected from H and D; and at least one of $R_1$, $R_2$, $R_3$, $R_4$, and $R_5$ is D;

in free or salt form.

Further provided are compounds of Formula I as follows:

1.1 Formula I, wherein the compound is in pharmaceutically acceptable salt form.

1.2 Formula I, wherein the compound is in free form.

1.3 Any of Formula I, 1.1, or 1.2, wherein each of $R_1$, $R_2$, $R_3$, $R_4$, and $R_5$ are D.

1.4 Any of Formula I or 1.1-1.3, wherein the compound is:

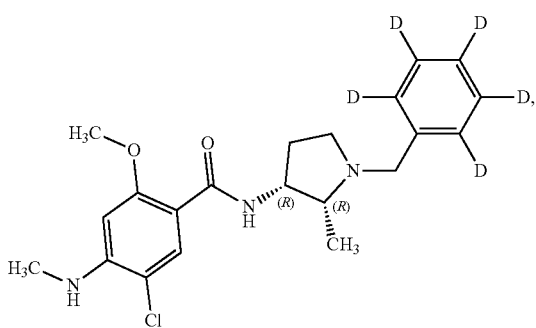

in free or salt form, e.g., in free or pharmaceutically acceptable salt form, e.g., in free form.

1.5 Any of Formula I or 1.1-1.4, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

1.6 Any of Formula I or 1.1-1.5, wherein the compound, in free or salt form (e.g., pharmaceutically acceptable salt form), has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Formula I or 1.1-1.5, wherein the compound, in free or salt form (e.g., pharmaceutically acceptable salt form), has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

1.7 Any of Formula I or 1.1-1.6, wherein the compound is substantially stereoisomerically pure. For instance, wherein the compound has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the compound is substantially diastereomerically and/or enantiomerically pure, e.g., wherein the compound is substantially diastereomerically and enantiomerically pure.

1.8 Any of Formula I or 1.1-1.7, wherein the compound is substantially diastereomerically pure. For instance, wherein the compound has a diastereomeric excess of greater than 90%, e.g., a diastereomeric excess equal to or greater than 95%, e.g., a diastereomeric excess equal to or greater than 96%, e.g., a diastereomeric excess equal to or greater than 97%, e.g., a diastereomeric excess equal to or greater than 98%, e.g., a diastereomeric excess equal to or greater than 99%.

1.9 Any of Formula I or 1.1-1.8, wherein the compound is substantially enantiomerically pure. For instance, wherein the compound has an enantiomeric excess of greater than 90%, e.g., an enantiomeric excess equal to or greater than 95%, e.g., an enantiomeric excess equal to or greater than 96%, e.g., an enantiomeric excess equal to or greater than 97%, e.g., an enantiomeric excess equal to or greater than 98%, e.g., an enantiomeric excess equal to or greater than 99%.

1.10 Any of Formula I or 1.1-1.9, wherein the compound has the stereochemical configuration as shown in Formula I.

1.11 Any of Formula I or 1.1-1.10, wherein the compound is in a pharmaceutical composition with a pharmaceutically acceptable carrier. For instance, any of Formula I or 1.1-1.10, wherein an effective amount of the compound is in a pharmaceutical composition with a pharmaceutically acceptable carrier.

Further provided is a compound of Formula II:

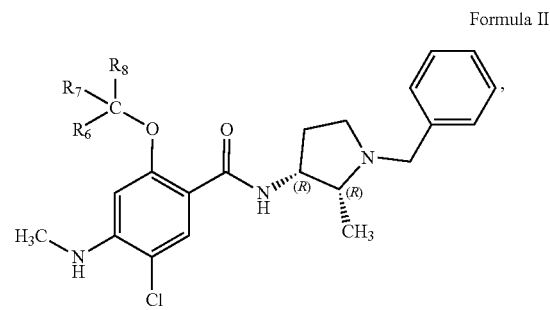

wherein:

$R_6$, $R_7$, and $R_8$ are independently selected from H and D; and at least one of $R_6$, $R_7$, and $R_8$ is D;

in free or salt form, wherein the compound is substantially free of its (S,S) enantiomer.

Further provided are compounds of Formula II as follows:

2.1 Formula II, wherein the compound is in pharmaceutically acceptable salt form.

2.2 Formula II, wherein the compound is in free form.

2.3 Any of Formula II, 2.1, or 2.2, wherein each of $R_6$, $R_7$, and $R_8$ are D.

2.4 Any of Formula II or 2.1-2.3, wherein the compound is:

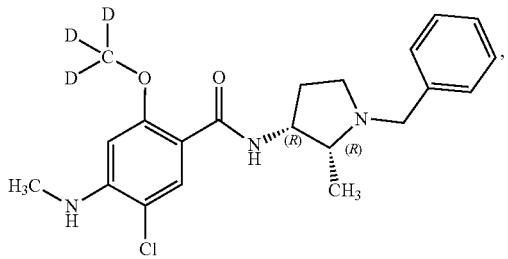

in free or salt form, e.g., in free or pharmaceutically acceptable salt form, e.g., in free form.

2.5 Any of Formula II or 2.1-2.4, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

2.6 Any of Formula II or 2.1-2.5, wherein the compound, in free or salt form (e.g., pharmaceutically acceptable salt form), has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Formula II or 2.1-2.5, wherein the compound, in free or salt form (e.g., pharmaceutically acceptable salt form), has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

2.7 Any of Formula II or 2.1-2.6, wherein the compound is substantially stereoisomerically pure. For instance, wherein the compound has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the compound is substantially diastereomerically and/or enantiomerically pure, e.g., wherein the compound is substantially diastereomerically and enantiomerically pure.

2.8 Any of Formula II or 2.1-2.7, wherein the compound is substantially diastereomerically pure. For instance, wherein the compound has a diastereomeric excess of greater than 90%, e.g., a diastereomeric excess equal to or greater than 95%, e.g., a diastereomeric excess equal to or greater than 96%, e.g., a diastereomeric excess equal to or greater than 97%, e.g., a diastereomeric excess equal to or greater than 98%, e.g., a diastereomeric excess equal to or greater than 99%.

2.9 Any of Formula II or 2.1-2.8, wherein the compound is substantially enantiomerically pure. For instance, wherein the compound has an enantiomeric excess of greater than 90%, e.g., an enantiomeric excess equal to or greater than 95%, e.g., an enantiomeric excess equal to or greater than 96%, e.g., an enantiomeric excess equal to or greater than 97%, e.g., an enantiomeric excess equal to or greater than 98%, e.g., an enantiomeric excess equal to or greater than 99%.

2.10 Any of Formula II or 2.1-2.9, wherein the compound has the stereochemical configuration as shown in Formula II.

2.11 Any of Formula II or 2.1-2.10, wherein the compound is in a pharmaceutical composition with a pharmaceutically acceptable carrier. For instance, any of Formula II or 2.1-2.10, wherein an effective amount of the compound is in a pharmaceutical composition with a pharmaceutically acceptable carrier.

Further provided is a pharmaceutical composition (Composition 1) comprising a compound of Formula I (e.g., any of Formula 1.1-1.11):

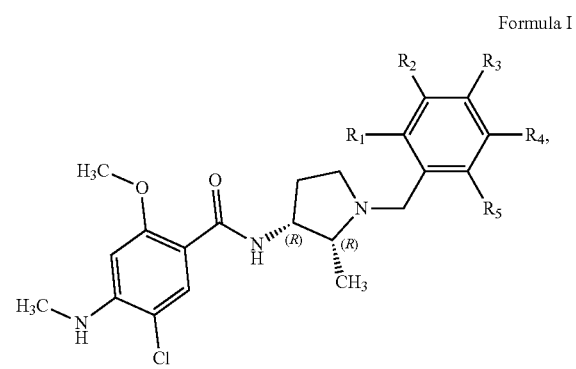

Formula I wherein:
$R_1$, $R_2$, $R_3$, $R_4$, and $R_5$ are independently selected from H and D; and
at least one of $R_1$, $R_2$, $R_3$, $R_4$, and $R_5$ is D;
in free or pharmaceutically acceptable salt form.

Further provided is a pharmaceutical composition (Composition 2) comprising a compound of Formula II (e.g., any of Formula 2.1-2.11):

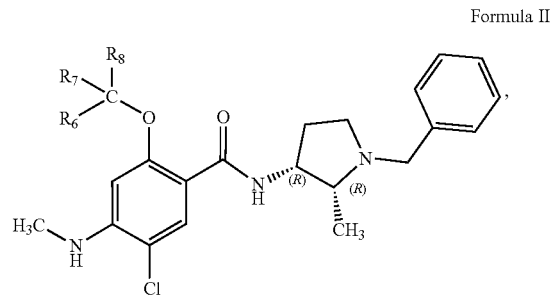

Formula II wherein:
$R_6$, $R_7$, and $R_8$ are independently selected from H and D; and
at least one of $R_6$, $R_7$, and $R_8$ is D;
in free or pharmaceutically acceptable salt form,
wherein the compound is substantially free of its (S,S) enantiomer.

Further provided are Composition 1 and Composition 2 as follows:

1.1 Composition 1 or Composition 2, wherein the composition comprises a pharmaceutically acceptable carrier.

1.2 Composition 1, 2, or 1.1, wherein the composition comprises the compound, in free or pharmaceutically acceptable salt form, as described in any of Formula I or 1.1-1.11 vide supra. Or, Composition 1, 2, or 1.1, wherein the composition comprises the compound, in free or pharmaceutically acceptable salt form, as described in any of Formula II or 2.1-2.11 vide supra.

1.3 Any of Composition 1, 2, 1.1, or 1.2, wherein the compound is in free form.

1.4 Any of Composition 1, 2, or 1.1-1.3, wherein the compound of Formula I is:

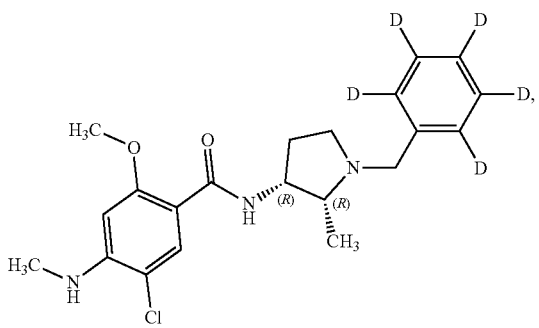

in free or pharmaceutically acceptable salt form, e.g., in free form.

1.5 Any of Composition 1, 2, or 1.1-1.3, wherein the compound of Formula II is:

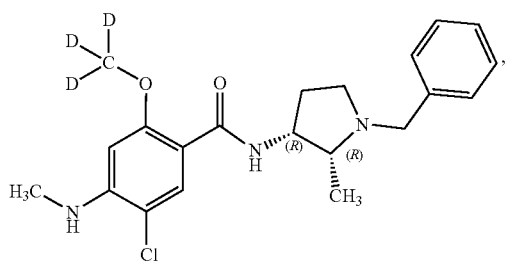

in free or pharmaceutically acceptable salt form, e.g., in free form.

1.6 Any of Composition 1, 2, or 1.1-1.5, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

1.7 Any of Composition 1 or 1.1-1.6, wherein the compound of Formula I, in free or pharmaceutically acceptable salt form, has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Composition 1 or 1.1-1.6, wherein the compound of Formula I, in free or pharmaceutically acceptable salt form, has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%. Or, any of Composition 2 or 1.1-1.6, wherein the compound of Formula II, in free or pharmaceutically acceptable salt form, has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Composition 2 or 1.1-1.6, wherein the compound of Formula II, in free or pharmaceutically acceptable salt form, has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

1.8 Any of Composition 1, 2, or 1.1-1.7, wherein the composition is in oral or parenteral dosage form, e.g., oral dosage form, for instance, a tablet, capsule, solution, or suspension, for instance, a capsule or tablet.

1.9 Any of Composition 1 or 1.1-1.8, wherein the composition comprises a therapeutically effective amount of the compound of Formula I, in free or pharmaceutically acceptable salt form, e.g., a therapeutically effective amount of the compound of Formula I, in free or pharmaceutically acceptable salt form, for the prophylaxis or treatment of a disorder disclosed herein, e.g., a therapeutically effective amount of the compound of Formula I, in free or pharmaceutically acceptable salt form, for use in any of the methods disclosed herein. Or, any of Composition 2 or 1.1-1.8, wherein the composition comprises a therapeutically effective amount of the compound of Formula II, in free or pharmaceutically acceptable salt form, e.g., a therapeutically effective amount of the compound of Formula II, in free or pharmaceutically acceptable salt form, for the prophylaxis or treatment of a disorder disclosed herein, e.g., a therapeutically effective amount of the compound of Formula II, in free or pharmaceutically acceptable salt form, for use in any of the methods disclosed herein.

1.10 Any of Composition 1 or 1.1-1.9, wherein the composition is substantially free of any other stereoisomeric form of Formula I. For instance, any of Composition 1 or 1.1-1.9, wherein the composition is substantially free of any other diastereomeric and/or enantiomeric form of Formula I, e.g., wherein the composition is substantially free of any other diastereomeric and enantiomeric form of Formula I. Or, any of Composition 2 or 1.1-1.9, wherein the composition is substantially free of any other stereoisomeric form of Formula II. For instance, any of Composition 2 or 1.1-1.9, wherein the composition is substantially free of any other diastereomeric and/or enantiomeric form of Formula II, e.g., wherein the composition is substantially free of any other diastereomeric and enantiomeric form of Formula II.

1.11 Any of Composition 1 or 1.1-1.10, wherein the composition comprises less than 10% w/w (weight/weight) of any other stereoisomeric form of Formula I, e.g., less than 5% w/w of any other stereoisomeric form of Formula I, e.g., less than 4% w/w of any other stereoisomeric form of Formula I, e.g., less than 3% w/w of any other stereoisomeric form of Formula I, e.g., less than 2% w/w of any other stereoisomeric form of Formula I, e.g., less than 1% w/w of any other stereoisomeric form of Formula I. Or, any of Composition 2 or 1.1-1.10, wherein the composition comprises less than 10% w/w (weight/weight) of any other stereoisomeric form of Formula II, e.g., less than 5% w/w of any other stereoisomeric form of Formula II, e.g., less than 4% w/w of any other stereoisomeric form of Formula II, e.g., less than 3% w/w of any other stereoisomeric form of Formula II, e.g., less than 2% w/w of any other stereoisomeric form of Formula II, e.g., less than 1% w/w of any other stereoisomeric form of Formula II.

1.12 Any of Composition 1 or 1.1-1.11, wherein the composition comprises less than 10% w/w of any other diastereomeric form of Formula I, e.g., less than 5% w/w of any other diastereomeric form of Formula I, e.g., less than 4% w/w of any other diastereomeric form of Formula I, e.g., less than 3% w/w of any other diastereomeric form of Formula I, e.g., less than 2% w/w of any other diastereomeric form of Formula I, e.g., less than 1% w/w of any other diastereomeric form of Formula I. Or, any of Composition 2 or 1.1-1.11, wherein the composition comprises less than 10% w/w of any other diastereomeric form of Formula II, e.g., less than 5% w/w of any other diastereomeric form of Formula II, e.g., less than 4% w/w of any other diastereomeric form of Formula II, e.g., less than 3% w/w of any other diastereomeric form of Formula II, e.g., less than 2% w/w of any other diastereomeric form of Formula II, e.g., less than 1% w/w of any other diastereomeric form of Formula II.

1.13 Any of Composition 1 or 1.1-1.12, wherein the composition comprises less than 10% w/w of any other enantiomeric form of Formula I, e.g., less than 5% w/w of any other enantiomeric form of Formula I, e.g., less than 4% w/w of any other enantiomeric form of Formula I, e.g., less than 3% w/w of any other enantiomeric form of Formula I, e.g., less than 2% w/w of any other enantiomeric form of Formula I, e.g., less than 1% w/w of any other enantiomeric form of Formula I. Or, any of Composition 2 or 1.1-1.12, wherein the composition comprises less than 10% w/w of any other enantiomeric form of Formula II, e.g., less than 5% w/w of any other enantiomeric form of Formula II, e.g., less than 4% w/w of any other enantiomeric form of Formula II, e.g., less than 3% w/w of any other enantiomeric form of Formula II, e.g., less than 2% w/w of any other enantiomeric form of Formula II, e.g., less than 1% w/w of any other enantiomeric form of Formula II.

1.14 Any of Composition 1 or 1.1-1.13, wherein the compound has the stereochemical configuration as shown in Formula I. Or, any of Composition 2 or 1.1-1.13, wherein the compound has the stereochemical configuration as shown in Formula II.

1.15 Any of Composition 1 or 1.1-1.14, wherein the composition comprises 1-60 mg of the compound of Formula I, in free or pharmaceutically acceptable salt form. For instance, any of Composition 1 or 1.1-1.14, wherein the composition comprises 1-10 mg, e.g., 1-9 mg (e.g., 1-8 mg) of the compound of Formula I, in free or pharmaceutically acceptable salt form. For instance, any of Composition 1 or 1.1-1.14, wherein the composition comprises 3 mg or 10 mg of the compound of Formula I, in free or pharmaceutically acceptable salt form. For instance, any of Composition 1 or 1.1-1.14, wherein the composition comprises 1 mg to less than 3 mg (e.g., 2 mg) of the compound of Formula I, in free or pharmaceutically acceptable salt form. Or, any of Composition 2 or 1.1-1.14, wherein the composition comprises 1-60 mg of the compound of Formula II, in free or pharmaceutically acceptable salt form. For instance, any of Composition 2 or 1.1-1.14, wherein the composition comprises 1-10 mg, e.g., 1-9 mg (e.g., 1-8 mg) of the compound of Formula II, in free or pharmaceutically acceptable salt form. For instance, any of Composition 2 or 1.1-1.14, wherein the composition comprises 3 mg or 10 mg of the compound of Formula II, in free or pharmaceutically acceptable salt form. For instance, any of Composition 2 or 1.1-1.14, wherein the composition comprises 1 mg to less than 3 mg (e.g., 2 mg) of the compound of Formula II, in free or pharmaceutically acceptable salt form.

1.16 Any of Composition 1, 2, or 1.1-1.15, wherein the composition is for once, twice, or three times daily dosing. For instance, any of Composition 1, 2, or 1.1-1.15, wherein the composition is for once daily dosing.

Further provided are methods of prophylaxis or treatment of a central nervous system disorder (e.g., a brain disorder), for instance, a central nervous system disorder (e.g., a brain disorder) that benefits from modulating dopamine and/or serotonin transmission, in a patient (e.g., a human) in need thereof, wherein the method comprises administering to the patient a compound of Formula I, in free or pharmaceutically acceptable salt form (e.g., any of Formula I or 1.1-1.11 vide supra), or a compound of Formula II, in free or pharmaceutically acceptable salt form (e.g., any of Formula II or 2.1-2.11), or a pharmaceutical composition comprising a compound of Formula I, in free or pharmaceutically acceptable salt form (e.g., Formula 1.11 or any of Composition 1 or 1.1-1.16 vide supra), or a pharmaceutical composition comprising a compound of Formula II, in free or pharmaceutically acceptable salt form (e.g., Formula 2.11 or any of Composition 2 or 1.1-1.16 vide supra). Further provided are methods of prophylaxis or treatment of a central nervous system disorder (e.g., a brain disorder) that benefits from D2 receptor antagonism, D3 receptor antagonism, D4 receptor antagonism, 5-HT1A receptor agonism (e.g., 5-HT1A receptor partial agonism), and/or 5-HT2A receptor agonism in a patient (e.g., a human) in need thereof, wherein the method comprises administering to the patient a compound of Formula I, in free or pharmaceutically acceptable salt form (e.g., any of Formula I or 1.1-1.11 vide supra), or a compound of Formula II, in free or pharmaceutically acceptable salt form (e.g., any of Formula II or 2.1-2.11 vide supra), or a pharmaceutical composition comprising a compound of Formula I, in free or pharmaceutically acceptable salt form (e.g., Formula 1.11 or any of Composition 1 or 1.1-1.16 vide supra), or a pharmaceutical composition comprising a compound of Formula II, in free or pharmaceutically acceptable salt form (e.g., Formula 2.11 or any of Composition 2 or 1.1-1.16 vide supra). For instance, provided are methods as described below.

Further provided are methods of enhancing neural plasticity in a patient (e.g., a human) in need thereof, wherein the method comprises administering to the patient a compound of Formula I, in free or pharmaceutically acceptable salt form (e.g., any of Formula I or 1.1-1.11 vide supra), or a compound of Formula II, in free or pharmaceutically acceptable salt form (e.g., any of Formula II or 2.1-2.11), or a pharmaceutical composition comprising a compound of Formula I, in free or pharmaceutically acceptable salt form (e.g., Formula 1.11 or any of Composition 1 or 1.1-1.16 vide supra), or a pharmaceutical composition comprising a compound of Formula II, in free or pharmaceutically acceptable salt form (e.g., Formula 2.11 or any of Composition 2 or 1.1-1.16 vide supra). For instance, provided are methods of enhancing neural plasticity to improve recovery in a patient (e.g., a human) in need thereof with a brain injury, e.g., to improve recovery following a stroke or traumatic brain injury, wherein the method comprises administering to the patient a compound of Formula I, in free or pharmaceutically acceptable salt form (e.g., any of Formula I or 1.1-1.11 vide supra), or a compound of Formula II, in free or pharmaceutically acceptable salt form (e.g., any of Formula II or 2.1-2.11), or a pharmaceutical composition comprising a compound of Formula I, in free or pharmaceutically acceptable salt form (e.g., Formula 1.11 or any of Composition 1 or 1.1-1.16 vide supra), or a pharmaceutical composition comprising a compound of Formula II, in free or pharmaceutically acceptable salt form (e.g., Formula 2.11 or any of Composition 2 or 1.1-1.16 vide supra).

Provided is a method (Method 1) for treatment or prophylaxis of a disorder (e.g., a brain disorder) in a patient (e.g., a human) in need thereof, wherein the method comprises administering to the patient an effective amount of a compound of Formula I:

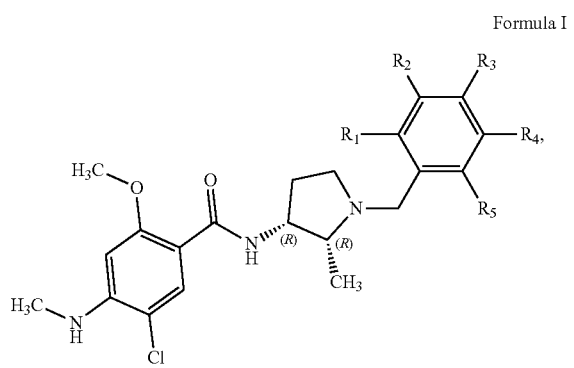

Formula I wherein:
$R_1$, $R_2$, $R_3$, $R_4$, and $R_5$ are independently selected from H and D; and
at least one of $R_1$, $R_2$, $R_3$, $R_4$, and $R_5$ is D;
in free or pharmaceutically acceptable salt form.

Further provided is a method (Method 2) for treatment or prophylaxis of a disorder (e.g., a brain disorder) in a patient (e.g., a human) in need thereof, wherein the method comprises administering to the patient an effective amount of a compound of Formula II:

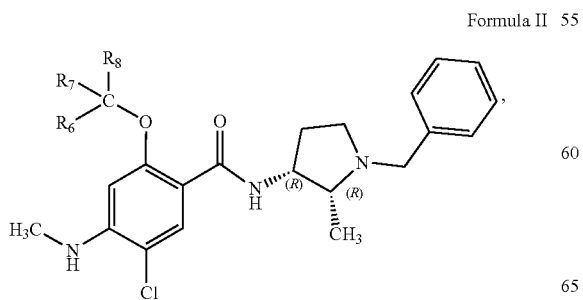

Formula II wherein:
$R_6$, $R_7$, and $R_8$ are independently selected from H and D; and
at least one of $R_6$, $R_7$, and $R_8$ is D;
in free or pharmaceutically acceptable salt form,
wherein the effective amount of the compound is substantially free of its (S,S) enantiomer.

Further provided are Method 1 and Method 2 as follows:
1.1 Method 1, wherein the method comprises administering to the patient a compound of Formula I, in free or pharmaceutically acceptable salt form, as described in any of Formula I or 1.1-1.11 vide supra. For instance, Method 1, wherein the method comprises administering to the patient a pharmaceutical composition comprising a compound of Formula I, in free or pharmaceutically acceptable salt form, as described in any of Formula 1.11 or Composition 1 or 1.1-1.16 vide supra.
1.2 Method 2, wherein the method comprises administering to the patient a compound of Formula II, in free or pharmaceutically acceptable salt form, as described in any of Formula II or 2.1-2.11 vide supra. For instance, Method 2, wherein the method comprises administering to the patient a pharmaceutical composition comprising a compound of Formula II, in free or pharmaceutically acceptable salt form, as described in any of Formula 2.11 or Composition 2 or 1.1-1.16 vide supra.
1.3 Method 1 or 1.1, wherein the effective amount of the compound of Formula I, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of the compound of Formula I, in free or pharmaceutically acceptable salt form, is substantially diastereomerically and/or enantiomerically pure, e.g., wherein the effective amount of the compound of Formula I, in free or pharmaceutically acceptable salt form, is substantially diastereomerically and enantiomerically pure. For instance, wherein the effective amount of the compound of Formula I, in free or pharmaceutically acceptable salt form, has a diastereomeric and/or enantiomeric excess of greater than 90%, e.g., a diastereomeric and/or enantiomeric excess equal to or greater than 95%, a diastereomeric and/or enantiomeric excess equal to or greater than 96%, a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of the compound of Formula I, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.
1.4 Method 2 or 1.2, wherein the effective amount of the compound of Formula II, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of the compound of Formula II, in free or pharmaceutically acceptable salt form, is substantially diastereomerically and/or enantiomerically pure, e.g., wherein the effective amount of the compound of Formula II, in free or pharmaceutically acceptable salt form, is substantially diastereomerically and enantiomerically pure. For instance, wherein the effective amount of the compound of Formula II, in free or pharmaceutically acceptable salt form, has a diastereomeric and/or enantiomeric excess of greater than 90%, e.g., a diastereomeric and/or enantiomeric excess equal to or greater than 95%, a diastereomeric and/or enantiomeric excess equal to or greater than 96%, a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of the compound of Formula II, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.

1.5 Any of Method 1, 2, or 1.1-1.4, wherein the compound is in free form.

1.6 Any of Method 1, 1.1, 1.3, or 1.5, wherein the method comprises administering an effective amount of Compound A:

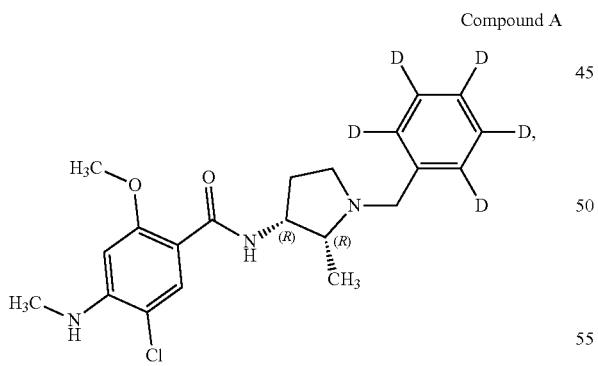

Compound A in free or pharmaceutically acceptable salt form, e.g., in free form.

1.7 Method 1.6, wherein the effective amount Compound A, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of Compound A, in free or pharmaceutically acceptable salt form, is substantially diastereomerically and/or enantiomerically pure, e.g., wherein the effective amount of Compound A, in free or pharmaceutically acceptable salt form, is substantially diastereomerically and enantiomerically pure. For instance, wherein the effective amount of Compound A, in free or pharmaceutically acceptable salt form, has a diastereomeric and/or enantiomeric excess of greater than 90%, e.g., a diastereomeric and/or enantiomeric excess equal to or greater than 95%, e.g., a diastereomeric and/or enantiomeric excess equal to or greater than 96%, e.g., a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of Compound A, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.

1.8 Any of Method 2, 1.2, 1.4, or 1.5, wherein the method comprises administering an effective amount of Compound B:

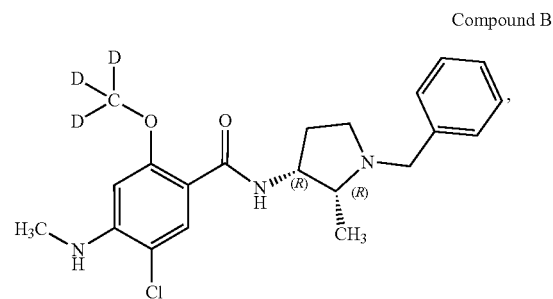

Compound B in free or pharmaceutically acceptable salt form, e.g., in free form.

1.9 Method 1.8, wherein the effective amount Compound B, in free or pharmaceutically acceptable salt form, has a stereoisomeric excess of greater than 90%, e.g., a stereoisomeric excess equal to or greater than 95%, e.g., a stereoisomeric excess equal to or greater than 96%, e.g., a stereoisomeric excess equal to or greater than 97%, e.g., a stereoisomeric excess equal to or greater than 98%, e.g., a stereoisomeric excess equal to or greater than 99%. For instance, wherein the effective amount of Compound B, in free or pharmaceutically acceptable salt form, is substantially diastereomerically and/or enantiomerically pure, e.g., wherein the effective amount of Compound B, in free or pharmaceutically acceptable salt form, is substantially diastereomerically and enantiomerically pure. For instance, wherein the effective amount of Compound B, in free or pharmaceutically acceptable salt form, has a diastereomeric and/or enantiomeric excess of greater than 90%, e.g., a diastereomeric and/or enantiomeric excess equal to or greater than 95%, e.g., a diastereomeric and/or enantiomeric excess equal to or greater than 96%, e.g., a diastereomeric and/or enantiomeric excess equal to or greater than 97%, e.g., a diastereomeric and/or enantiomeric excess equal to or greater than 98%, e.g., a diastereomeric and/or enantiomeric excess equal to or greater than 99%. For instance, wherein the effective amount of Compound B, in free or pharmaceutically acceptable salt form, has a diastereomeric and enantiomeric excess of greater than 90%, e.g., a diastereomeric and enantiomeric excess equal to or greater than 95%, e.g., a diastereomeric and enantiomeric excess equal to or greater than 96%, e.g., a diastereomeric and enantiomeric excess equal to or greater than 97%, e.g., a diastereomeric and enantiomeric excess equal to or greater than 98%, e.g., a diastereomeric and enantiomeric excess equal to or greater than 99%.

1.10 Any of Method 1, 2, or 1.1-1.9, wherein the designation of deuterium (i.e., D) at a position means that position has a significantly greater than natural abundance of deuterium at that position (e.g., greater than 0.1%, or greater than 0.5%, or greater than 1%, or greater than 5%). Any atom not designated as a particular isotope is present at natural isotopic abundance.

1.11 Any of Method 1, 2, or 1.1-1.10, wherein the effective amount of the compound, in free or pharmaceutically acceptable salt form, has greater than 50% incorporation of deuterium (i.e., D) at one or more positions (e.g., at all positions) designated as deuterium (i.e., D), e.g., greater than 60%, or greater than 70%, or greater than 80%, or greater than 90%, or greater than 95%, or greater than 96%, or greater than 97%, or greater than 98%, or greater than 99%. For instance, any of Method 1, 2, or 1.1-1.10, wherein the effective amount of the compound, in free or pharmaceutically acceptable salt form, has greater than 50% incorporation of deuterium (i.e., D) at each position designated as deuterium (i.e., D), e.g., greater than 60%, or greater than 70%, or greater than 80%, or greater than 90%, or greater than 95%, or greater than 96%, or greater than 97%, or greater than 98%, or greater than 99%.

1.12 Any of Method 1, 2, or 1.1-1.11, wherein the disorder is a brain disorder. For instance, any of Method 1, 2, or 1.1-1.11, wherein the disorder is a neuropsychiatric condition in which anhedonia is prominent.

1.13 Any of Method 1, 2, or 1.1-1.12, wherein the disorder is an affective (mood) disorder or an anxiety disorder.

1.14 Any of Method 1, 2, or 1.1-1.13, wherein the disorder is depression (e.g., depression associated with anhedonia), an anxiety disorder, psychosis (e.g., psychosis in neurodegenerative conditions, such as psychosis in Alzheimer's disease, Parkinson's disease, or dementia (e.g., dementia-related psychosis)), schizophrenia, schizoaffective disorder, post-traumatic stress disorder (PTSD), attention-deficit/hyperactivity disorder (ADHD), Tourette syndrome, anorexia nervosa, bulimia nervosa, binge-eating disorder, body dysmorphic disorder, obsessive compulsive disorder, addiction, bipolar disorder (including bipolar depression, bipolar mania, and bipolar disorder with mixed features), or a migraine. For instance, any of Method 1, 2, or 1.1-1.13, wherein the anxiety disorder is panic disorder, social anxiety disorder, a phobia, or generalized anxiety disorder. Or, any of Method 1, 2, or 1.1-1.13, wherein the method is prophylaxis or treatment of behavioral and psychological symptoms of dementia including agitation, depression, anxiety, apathy, and/or psychosis. For instance, any of Method 1, 2, or 1.1-1.13, wherein the method is prophylaxis or treatment of post-traumatic stress disorder (PTSD), e.g., treatment of post-traumatic stress disorder (PTSD).

1.15 Any of Method 1, 2, or 1.1-1.14, wherein the disorder is anhedonia or depression associated with anhedonia, suicidal ideation, anxious depression, inflammatory depression, treatment-resistant depression, dysthymia, bipolar depression, psychotic depression, or post-psychotic depression. For instance, any of Method 1, 2, or 1.1-1.14, wherein the disorder is anxious depression. Or, for instance any of Method 1, 2, or 1.1-1.14, wherein the disorder is melancholic depression.

1.16 Any of Method 1, 2, or 1.1-1.15, wherein the disorder is major depressive disorder.

1.17 Any of Method 1, 2, or 1.1-1.14, wherein the disorder is a substance use disorder.

1.18 Any of Method 1, 2, or 1.1-1.14, wherein the method is prophylaxis or treatment of negative symptoms of schizophrenia. Or, any of Method 1, 2, or 1.1-1.14, wherein the method is improving cognition in schizophrenia.

1.19 Any of Method 1, 2, or 1.1-1.14, wherein the method is improving cognition, e.g., in cognitive impairment, e.g., cognitive impairment in schizophrenia, depression, or dementia. For instance, any of Method 1, 2, or 1.1-1.14, wherein the method is improving cognition in major depressive disorder.

1.20 Any of Method 1, 2, or 1.1-1.11, wherein the compound, in free or pharmaceutically acceptable salt form, is administered as an anti-emetic.

1.21 Any of Method 1, 2, or 1.1-1.20, wherein the method comprises administering 9-60 mg a day of the compound, in free or pharmaceutically acceptable salt form (i.e., 9-60 mg total daily dose of the compound, in free or pharmaceutically acceptable salt form). For instance, any of Method 1, 2, or 1.1-1.20, wherein the method comprises administering 9-36 mg a day of the compound, in free or pharmaceutically acceptable salt form (i.e., 9-36 mg total daily dose of the compound, in free or pharmaceutically acceptable salt form).

1.22 Any of Method 1, 2, or 1.1-1.21, wherein the method comprises administering an amount of the compound, in free or pharmaceutically acceptable salt form, that provides 55%-80% D2/D3 receptor occupancy, e.g., as measured by positron emission tomography. For instance, wherein the method comprises administering an amount of the compound, in free or pharmaceutically acceptable salt form, that provides about 65% D2/D3 receptor occupancy, e.g., as measured by positron emission tomography. Or, for instance, wherein the method comprises administering an amount of the compound, in free or pharmaceutically acceptable salt form, that provides about 60% D2/D3 receptor occupancy, e.g., as measured by positron emission tomography.

1.23 Method 1.21 or 1.22, wherein the disorder is psychosis (e.g., psychosis in neurodegenerative conditions, such as Alzheimer's disease, Parkinson's disease, and dementia (e.g., dementia-related psychosis)), schizophrenia, schizoaffective disorder, or bipolar disorder (e.g., bipolar mania).

1.24 Method 1.21 or 1.22, wherein the method is prophylaxis or treatment of negative symptoms of schizophrenia. Or, Method 1.21 or 1.22, wherein the method is improving cognition in schizophrenia.

1.25 Any of Method 1, 2, or 1.1-1.20, wherein the method comprises administering 1-9 mg (e.g., 1-8 mg, e.g., 1.5-6 mg) a day of the compound, in free or pharmaceutically acceptable salt form (i.e., 1-9 mg total daily dose, e.g., 1-8 mg total daily dose, e.g., 1.5-6 mg total daily dose, of the compound, in free or pharmaceutically acceptable salt form). For instance, any of Method 1, 2, or 1.1-1.20, wherein the method comprises administering 1-8 mg a day of the compound, in free or pharmaceutically acceptable salt form (i.e., 1-8 mg total daily dose of the compound, in free or pharmaceutically acceptable salt form). For instance, any of Method 1, 2, or 1.1-1.20, wherein the method comprises administering 1-3 mg a day of the compound, in free or pharmaceutically acceptable salt form (i.e., 1-3 mg total daily dose of the compound, in free or pharmaceutically acceptable salt form). For instance, any of Method 1, 2, or 1.1-1.20, wherein the method comprises administering 1 mg to less than 3 mg a day (e.g., 2 mg a day) of the compound, in free or pharmaceutically acceptable salt form (i.e., 1 mg to less than 3 mg total daily dose of the compound, in free or pharmaceutically acceptable salt form).

1.26 Any of Method 1, 2, 1.1-1.20, or 1.25, wherein the method comprises administering an amount of the compound, in free or pharmaceutically acceptable salt form, that provides 10%-60% (e.g., 40%-60% or, e.g., 10%-55%, e.g., 10%-50%, e.g., 30%-50% or, e.g., 15%-50%, e.g., 15%-45%, e.g., 20%-40%, e.g., 10%-30%) D2/D3 receptor occupancy, e.g., as measured by positron emission tomography. Or, for instance, any of Method 1, 2, 1.1-1.20, or 1.25, wherein the method comprises administering an amount of the compound, in free or pharmaceutically acceptable salt form, that provides ≤40% (e.g., about 40%), e.g., <40% D2/D3 receptor occupancy, e.g., as measured by positron emission tomography.

1.27 Method 1.25 or 1.26, wherein the disorder is depression (e.g., depression associated with anhedonia), an anxiety disorder, post-traumatic stress disorder (PTSD), attention-deficit/hyperactivity disorder (ADHD), Tourette syndrome, anorexia nervosa, bulimia nervosa, binge-eating disorder, body dysmorphic disorder, obsessive compulsive disorder, addiction, bipolar disorder, bipolar disorder with mixed features, or a migraine. For instance, Method 1.25 or 1.26, wherein the anxiety disorder is panic disorder, social anxiety disorder, a phobia, or generalized anxiety disorder. Or, for instance, Method 1.25 or 1.26, wherein the disorder is post-traumatic stress disorder.

1.28 Any of Method 1.25-1.27, wherein the disorder is anhedonia or depression associated with anhedonia, suicidal ideation, anxious depression, inflammatory depression, treatment-resistant depression, dysthymia, bipolar depression, psychotic depression, or post-psychotic depression. For instance, wherein the disorder is anxious depression.

1.29 Any of Method 1.25-1.28, wherein the disorder is major depressive disorder.

1.30 Method 1.25 or 1.26, wherein the disorder is a substance use disorder.

1.31 Any of Method 1, 2, or 1.1-1.30, wherein the method comprises administering a pharmaceutical composition comprising the compound, in free or pharmaceutically acceptable salt form. For instance, any of Method 1, 2, or 1.1-1.30, wherein the method comprises administering Formula 1.11 or Formula 2.11 or any of Composition 1, 2, or 1.1-1.16 vide supra.

1.32 Any of Method 1, 2, or 1.1-1.31, wherein the method comprises administering the compound of Formula I, in free or pharmaceutically acceptable salt form, or the compound of Formula II, in free or pharmaceutically acceptable salt form, once, twice, or three times a day, e.g., once a day. For instance, any of Method 1, 2, or 1.1-1.31, wherein the method comprises administering a pharmaceutical composition comprising the compound of Formula I, in free or pharmaceutically acceptable salt form, or a pharmaceutical composition comprising the compound of Formula II, in free or pharmaceutically acceptable salt form, once, twice, or three times a day, e.g., once a day.

1.33 Any of Method 1, 2, or 1.1-1.32, wherein the method comprises administering Compound A, in free or pharmaceutically acceptable salt form, or Compound B, in free or pharmaceutically acceptable salt form, once, twice, or three times a day, e.g., once a day.

1.34 Also provided are any of Methods 1, 2, or 1.1-1.33 to promote or enhance neural plasticity in a patient (e.g., a human) in need thereof, wherein the method comprises administering to the patient a compound of Formula I, in free or pharmaceutically acceptable salt form (e.g., any of Formula I or 1.1-1.11 vide supra), or a compound of Formula II, in free or pharmaceutically acceptable salt form (e.g., any of Formula II or 2.1-2.11), or a pharmaceutical composition comprising a compound of Formula I, in free or pharmaceutically acceptable salt form (e.g., Formula 1.11 or any of Composition 1 or 1.1-1.16 vide supra), or a pharmaceutical composition comprising a compound of Formula II, in free or pharmaceutically acceptable salt form (e.g., Formula 2.11 or any of Composition 2 or 1.1-1.16 vide supra). For instance, provided are methods of promoting or enhancing neural plasticity to improve recovery in a patient (e.g., a human) in need thereof with a brain injury, e.g., to improve recovery following a stroke or traumatic brain injury, wherein the method comprises administering to the patient a compound of Formula I, in free or pharmaceutically acceptable salt form (e.g., any of Formula I or 1.1-1.11 vide supra), or a compound of Formula II, in free or pharmaceutically acceptable salt form (e.g., any of Formula II or 2.1-2.11), or a pharmaceutical composition comprising a compound of Formula I, in free or pharmaceutically acceptable salt form (e.g., Formula 1.11 or any of Composition 1 or 1.1-1.16 vide supra), or a pharmaceutical composition comprising a compound of Formula II, in free or pharmaceutically acceptable salt form (e.g., Formula 2.11 or any of Composition 2 or 1.1-1.16 vide supra).

Further provided is a compound of Formula I (e.g., any of Formula 1.1-1.11) or a pharmaceutical composition disclosed herein (e.g., Formula 1.11 or any of Composition 1 or 1.1-1.16) for use in any of Method 1 or 1.1-1.34 vide supra.

Further provided is a compound of Formula II (e.g., any of Formula 2.1-2.11) or a pharmaceutical composition disclosed herein (e.g., Formula 2.11 or any of Composition 2 or 1.1-1.15) for use in any of Method 2 or 1.1-1.34 vide supra.

Further provided is use of a compound of Formula I (e.g., any of Formula 1.1-1.11) or a pharmaceutical composition disclosed herein (e.g., Formula 1.11 or any of Composition 1 or 1.1-1.16) in any of Method 1 or 1.1-1.34 vide supra.

Further provided is use of a compound of Formula II (e.g., any of Formula 2.1-2.11) or a pharmaceutical composition disclosed herein (e.g., Formula 2.11 or any of Composition 2 or 1.1-1.16) in any of Method 2 or 1.1-1.34 vide supra.

Further provided is use of a compound of Formula I (e.g., any of Formula 1.1-1.11) in the manufacture of a medicament (e.g., Formula 1.11 or any of Composition 1 or 1.1-1.16) for use in any of Method 1 or 1.1-1.34 vide supra.

Further provided is use of a compound of Formula II (e.g., any of Formula 2.1-2.11) in the manufacture of a medicament (e.g., Formula 2.11 or any of Composition 2 or 1.1-1.16) for use in any of Method 2 or 1.1-1.34 vide supra.

Further provided are intermediate compounds of Formula III and Formula IV, each in free or salt (e.g., pharmaceutically acceptable salt) form.

For instance, further provided is a compound of Formula III:

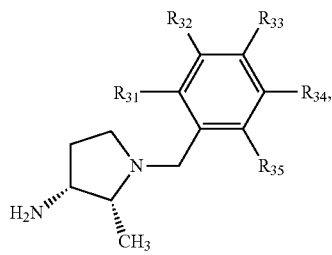

Formula III wherein:
$R_{31}$, $R_{32}$, $R_{33}$, $R_{34}$, and $R_{35}$ are independently selected from H and D; and
at least one of $R_{31}$, $R_{32}$, $R_{33}$, $R_{34}$, and $R_{35}$ is D;
in free or salt form.

Further provided are compounds of Formula III as follows:
3.1 Formula III, wherein the compound is in pharmaceutically acceptable salt form.
3.2 Formula III or 3.1, wherein each of $R_{31}$, $R_{32}$, $R_{33}$, $R_{34}$, and $R_{35}$ are D.
3.3 Formula III, 3.1, or 3.2, wherein the compound is:

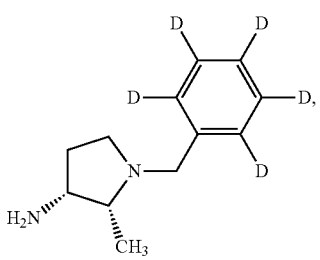

in free or salt (e.g., pharmaceutically acceptable salt) form, e.g., in free form.

Also further provided is a compound of Formula IV:

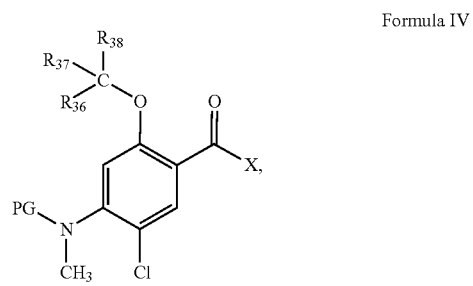

Formula IV wherein:
X is OH or a leaving group;
PG is H or an amine protecting group (e.g., an ester, which with the nitrogen to which it is attached forms a carbamate, e.g., tert-butyloxycarbonyl or carboxybenzyl, e.g., tert-butyloxycarbonyl);
$R_{36}$, $R_{37}$, and $R_{38}$ are independently selected from H and D; and
at least one of $R_{36}$, $R_{37}$, and $R_{38}$ is D;
in free or salt form.

Further provided are compounds of Formula IV as follows:
4.1 Formula IV, wherein the compound is in pharmaceutically acceptable salt form.
4.2 Formula IV or 4.1, wherein each of $R_{36}$, $R_{37}$, and $R_{38}$ are D.
4.3 Any of Formula IV, 4.1, or 4.2, wherein the compound is:

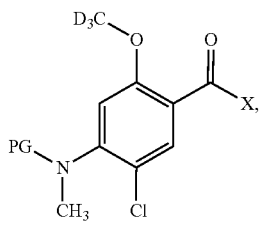

in free or salt (e.g., pharmaceutically acceptable salt) form, e.g., in free form.
4.4 Any of Formula IV or 4.1-4.3, wherein the compound is:

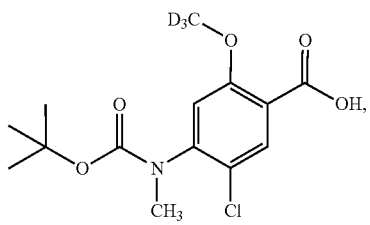 [SMILES: [2H]C([2H])([2H])Oc1cc(N(C)C(=O)OC(C)(C)C)c(Cl)cc1C(=O)O]

in free or salt (e.g., pharmaceutically acceptable salt) form, e.g., in free form.
4.5 Any of Formula IV or 4.1-4.4, wherein X is OH.
4.6 Any of Formula IV or 4.1-4.4, wherein X is a leaving group (e.g., an activated ester, e.g., an O-acylisourea, or a halide). For instance, any of Formula IV or 4.1-4.4, wherein the compound is:

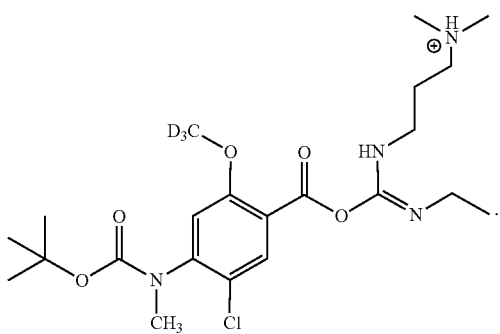 [SMILES: [2H]C([2H])([2H])Oc1cc(N(C)C(=O)OC(C)(C)C)c(Cl)cc1C(=O)O/C(=N/CC)NCCC[NH+](C)C]

Further provided is a process (Process 1) for synthesizing a compound of Formula I (e.g., any of Formula 1.1-1.11), in free or salt (e.g., pharmaceutically acceptable salt) form.

Further provided is Process 1 as follows:

1.1 Process 1, wherein the process comprises reacting a compound of Formula III (e.g., any of Formula 3.1-3.3) with a compound of Formula V:

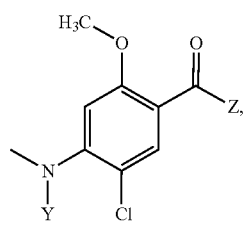

Formula V wherein:
Y is H or an amine protecting group (e.g., an ester, which with the nitrogen to which it is attached forms a carbamate, e.g., tert-butyloxycarbonyl or carboxybenzyl, e.g., tert-butyloxycarbonyl) and
Z is OH or a leaving group,
in free or pharmaceutically acceptable salt form.

1.2 Process 1 or 1.1, wherein Y is H.

1.3 Process 1 or 1.1, wherein Y is an amine protecting group. For instance, Process 1 or 1.1, wherein Y is tert-butyloxycarbonyl.

1.4 Any of Process 1 or 1.1-1.3, wherein Z is OH.

1.5 Any of Process 1 or 1.1-1.4, wherein the compound of Formula V is:

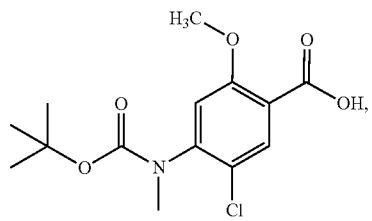 [SMILES: COc1cc(N(C)C(=O)OC(C)(C)C)c(Cl)cc1C(=O)O]

in free or salt (e.g., pharmaceutically acceptable salt) form, e.g., in free form.

1.6 Any of Process 1 or 1.1-1.3, wherein Z is a leaving group (e.g., an activated ester, e.g., an O-acylisourea, or a halide).

1.7 Any of Process 1, 1.1-1.3, or 1.6, wherein the compound of Formula V is:

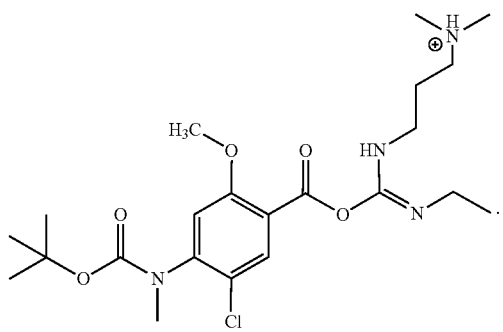 [SMILES: CC/N=C(\NCCC[NH+](C)C)OC(=O)c1cc(Cl)c(N(C)C(=O)OC(C)(C)C)cc1OC]

1.8 Any of Process 1 or 1.1-1.7, wherein the process occurs in the presence of an amine (e.g., triethylamine, e.g., triethylamine and dimethylformamide or dimethylacetamide).

1.9 Any of Process 1 or 1.1-1.8, wherein the process occurs in an organic solvent (e.g., triethylamine and dimethylacetamide).

1.10 Any of Process 1 or 1.1-1.9, wherein the process occurs with 1-ethyl-3-(3-dimethylaminopropyl) carbodiimide and hydroxybenzotriazole. For instance, any process wherein the process occurs with 1-ethyl-3-(3-dimethylaminopropyl) carbodiimide, hydroxybenzotriazole, triethylamine, and dimethylacetamide or dimethylformamide.

1.11 Any of Process 1 or 1.1-1.10, wherein the process comprises reacting

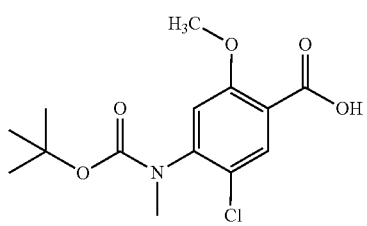 [SMILES: COc1cc(N(C)C(=O)OC(C)(C)C)c(Cl)cc1C(=O)O]

with an activating agent (e.g., 1-ethyl-3-(3-dimethylaminopropyl) carbodiimide), optionally wherein the product is formed in situ.

1.12 Any of Process 1 or 1.1-1.11, wherein the process further comprises removing the amine protecting group, e.g., under acidic or basic conditions, e.g., with HCl optionally in ethyl acetate.

1.13 Any of Process 1 or 1.1-1.12, wherein the process further comprises isolating the compound of Formula I (e.g., any of Formula 1.1-1.11), in free or salt (e.g., pharmaceutically acceptable salt) form.

Further provided is a process (Process 2) for synthesizing a compound of Formula II (e.g., any of Formula 2.1-2.11), in free or salt (e.g., pharmaceutically acceptable salt) form.

Further provided is Process 2 as follows:

2.1 Process 2, wherein the process comprises reacting a compound of Formula IV (e.g., any of Formula 4.1-4.6) with:

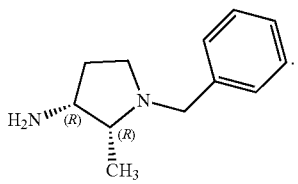

2.2 Process 2 or 2.1, wherein the process occurs in the presence of an amine (e.g., triethylamine, e.g., triethylamine and dimethylformamide or dimethylacetamide).

2.3 Process 2, 2.1, or 2.2, wherein the process occurs in an organic solvent (e.g., triethylamine and dimethylacetamide).

2.4 Any of Process 1 or 2.1-2.3, wherein the process occurs with 1-ethyl-3-(3-dimethylaminopropyl) carbodiimide and hydroxybenzotriazole. For instance, any process wherein the process occurs with 1-ethyl-3-(3-dimethylaminopropyl) carbodiimide, hydroxybenzotriazole, triethylamine, and dimethylacetamide or dimethylformamide.

2.5 Any of Process 2 or 2.1-2.4, wherein the process comprises reacting

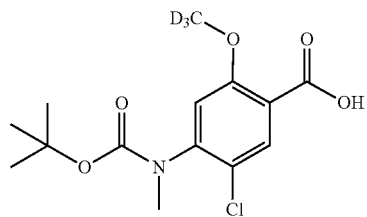 [SMILES: [2H]C([2H])([2H])Oc1cc(N(C)C(=O)OC(C)(C)C)c(Cl)cc1C(=O)O]

with an activating agent (e.g., 1-ethyl-3-(3-dimethylaminopropyl) carbodiimide), optionally wherein the product is formed in situ.

2.6 Any of Process 2 or 2.1-2.5, wherein the process further comprises removing the amine protecting group, e.g., under acidic or basic conditions, e.g., with HCl optionally in ethyl acetate.

2.7 Any of Process 2 or 2.1-2.6, wherein the process further comprises isolating the compound of Formula II (e.g., any of Formula 2.1-2.11), in free or salt (e.g., pharmaceutically acceptable salt) form.

For compounds disclosed herein, a hydrogen atom position of a structure is considered substituted with deuterium when the abundance of deuterium at that position is enriched. The natural abundance of deuterium is about 0.02%, so a compound is "enriched" with deuterium at a specific position when the frequency of incorporation of deuterium at that position exceeds 0.02%. Therefore, for deuterated compounds disclosed herein, any position designated as deuterium (i.e., D) may be enriched with deuterium at a level of greater than 0.1%, or greater than 0.5%, or greater than 1%, or greater than 5%, such as, greater than 50%, or greater than 60%, or greater than 70%, or greater than 80%, or greater than 90%, or greater than 95%, or greater than 96%, or greater than 97%, or greater than 98%, or greater than 99%. For compounds disclosed herein, any atom not designated as a particular isotope is present at natural isotopic abundance.

Compounds disclosed herein, e.g., any of Formula I (e.g., any of Formula 1.1-1.11), Formula II (e.g., any of Formula 2.1-2.11), Formula III (e.g., any of Formula 3.1-3.3), Formula IV (e.g., any of 4.1-4.6), Formula V, Compound A, and Compound B, may exist in free or salt form, e.g., as acid addition salts. As used herein, unless otherwise indicated, language such as "compound of formula" is to be understood as embracing the compound in any form, for example free or acid addition salt form, or where the compound contains an acidic substituent, in base addition salt form. Compounds of Formula I (e.g., any of Formula 1.1-1.11), Formula II (e.g., any of Formula 2.1-2.11), Compound A, and Compound B are intended for use as pharmaceuticals, therefore pharmaceutically acceptable salts are preferred. Salts which are unsuitable for pharmaceutical uses may be useful, for example, for the isolation or purification of free compounds of Formula I or Formula II or their pharmaceutically acceptable salts, so therefore are also included.

Isolation or purification of stereoisomers of any of the compounds disclosed herein, for instance, Formula I (e.g., any of Formula 1.1-1.11), Formula II (e.g., any of Formula 2.1-2.11), Formula III (e.g., any of 3.1-3.3), Formula IV (e.g., any of 4.1-4.6), Formula V, Compound A, and Compound B, any in free or pharmaceutically acceptable salt form, may be achieved by conventional methods known in the art, e.g., column purification, preparative thin layer chromatography, preparative HPLC, trituration, simulated moving beds, and the like.

Pure stereoisomeric forms of the compounds and intermediates disclosed herein are isomers substantially free of other enantiomeric and diastereomeric forms of the same basic molecular structure of said compounds or intermediates. "Substantially stereoisomerically pure" includes compounds or intermediates having a stereoisomeric excess of greater than 90% (i.e., more than 90% of one stereoisomer and less than 10% of any other possible stereoisomer). The terms "substantially diastereomerically pure" and "substantially enantiomerically pure" should be understood in a similar way, but then having regard to the diastereomeric excess and enantiomeric excess, respectively, of the material in question.

Compounds disclosed herein, e.g., any of Formula I (e.g., any of Formula 1.1-1.11), Formula II (e.g., any of Formula 2.1-2.11), Formula III (e.g., any of 3.1-3.3), Formula IV (e.g., any of 4.1-4.6), Formula V, Compound A, and Compound B, any in free or pharmaceutically acceptable salt form, may be made by using the methods as described and exemplified herein and by methods similar thereto and by methods known in the chemical art. Such methods include, but are not limited to, those described below. If not commercially available, starting materials for these processes may be made by procedures, which are selected from the chemical art using techniques that are similar to or analogous to the synthesis of known compounds.

Pharmaceutically acceptable salts of any of Formula I (e.g., any of Formula 1.1-1.11), Formula II (e.g., any of Formula 2.1-2.11), Formula III (e.g., any of 3.1-3.3), Formula IV (e.g., any of 4.1-4.6), Formula V, Compound A, and Compound B, may be synthesized from the parent compound which contains a basic or acidic moiety by conventional chemical methods. Generally, such salts can be prepared by reacting the free base forms of these compounds with a stoichiometric amount of the appropriate acid in an appropriate solvent.

For methods of treatment, the word "effective amount" is intended to encompass a therapeutically effective amount to treat a specific disease or disorder.

Dosages employed in practicing the present invention will of course vary depending, e.g. on the particular disease or condition to be treated, the particular compound used, the mode of administration, and the therapy desired.

Compounds disclosed herein, e.g., any of Formula I (e.g., any of Formula 1.1-1.11), Formula II (e.g., any of Formula 2.1-2.11), Compound A, or Compound B, any in free or pharmaceutically acceptable salt form, may be administered by any suitable route, including orally, parenterally, or transdermally, but are preferably administered orally.

Pharmaceutical compositions comprising compounds disclosed herein, e.g., any of Formula I (e.g., any of Formula 1.1-1.11 or any of Composition 1 or 1.1-1.16), any of Formula II (e.g., any of Formula 2.1-2.11 or any of Composition 2 or 1.1-1.16), Compound A, or Compound B, any in free or pharmaceutically acceptable salt form, may be prepared using conventional diluents or excipients and techniques known in the galenic art. Thus oral dosage forms may include tablets, capsules, solutions, suspensions, and the like.

"Patient" as used herein includes human and non-human (i.e., animal). In some embodiments, the patient is human.

EXAMPLES

Abbreviations

AcOH=acetic acid
Boc=tert-butyloxycarbonyl
DIAD=diisopropyl azodicarboxylate
DCM=dichloromethane
DMA or DMAc=dimethylacetamide
DMAP=4-dimethylaminopyridine
DMF=dimethylformamide
EDCI=1-ethyl-3-(3-dimethylaminopropyl) carbodiimide
EtOAc or EA=ethyl acetate
h=hour(s)
HOBt=hydroxybenzotriazole
MeOH=methanol
min=minute(s)
MsCl=methanesulfonyl chloride
rt (or RT or r.t.)=room temperature
TEA=triethylamine
TFA=trifluoroacetic acid
THF=tetrahydrofuran Example 1

Synthesis: 5-Chloro-N-((2R,3R)-1-((pentadeutero-phenyl)methyl)-2-methylpyrrolidin-3-yl)-2-methoxy-4-(methylamino)benzamide

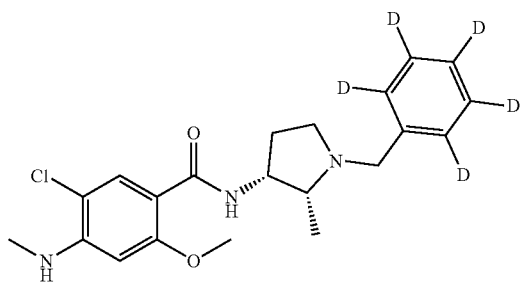 [SMILES: [2H]c1c([2H])c([2H])c(CN2CC[C@@H](NC(=O)c3cc(Cl)c(NC)cc3OC)[C@H]2C)c([2H])c1[2H]]

Step 1

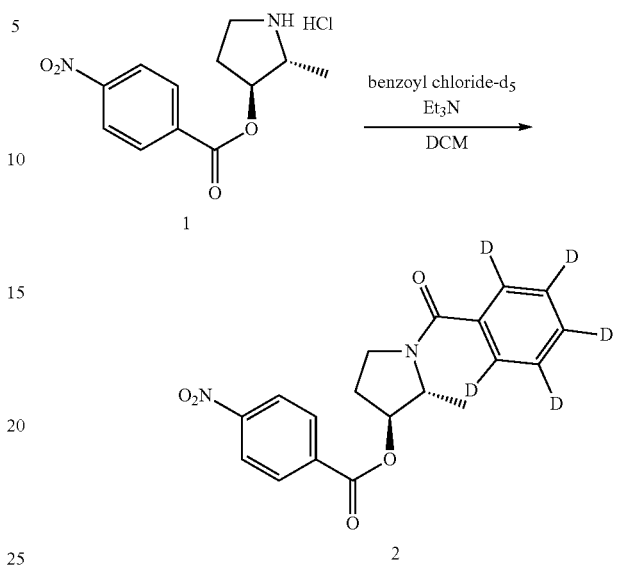

To a solution of 1 (8.0 g, 27.9 mmol) and benzoyl chloride-d5 (5.56 g, 38.2 mmol) in DCM (160 mL) is added Et$_3$N (12.7 g, 125 mmol) at 0° C. The reaction mixture is allowed to warm r.t. and stirred for 16 h. On completion, the reaction mixture is washed with water (90 mL×2), and concentrated to give 2 (8.75 g crude) as a white solid.

Step 2

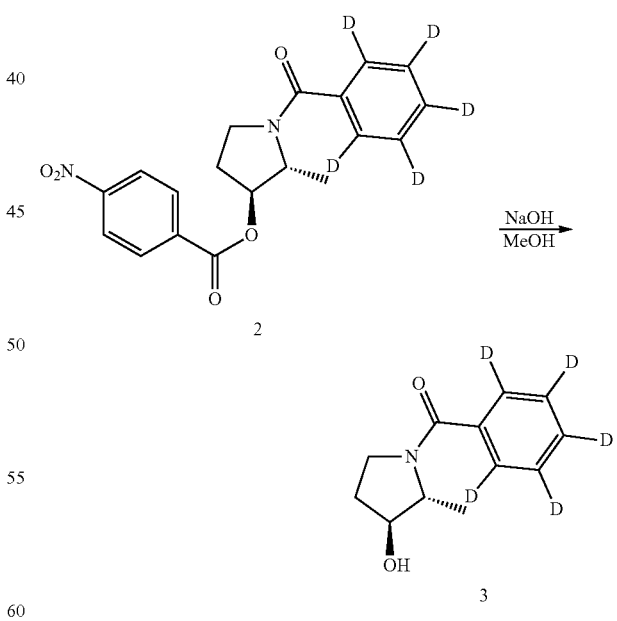

To a stirred solution of 2 (8.5 g, 23.65 mmol) in MeOH/H$_2$O (43 mL/43 mL) is added NaOH (1.14 g, 28.38 mmol). The reaction mixture is stirred for 2 h and then concentrated under reduced pressure. The residue is diluted with water (60 mL), extracted with DCM (60 mL×5). The organic phase is concentrated to give 3 (4.7 g crude) as a white solid.

Step 3

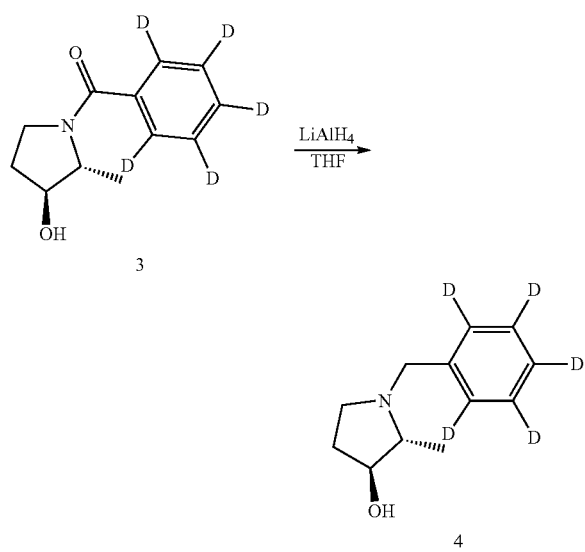

A solution of 3 (4.7 g, 22.35 mmol) in dry THF (47 mL) is added dropwise to a stirring solution of LiAlH$_4$ (2.1 g, 55.88 mmol) in dry THF (47 mL) at 0~10° C. under nitrogen atmosphere. After stirring at 0~10° C. for 45 min, the reaction is allowed to warm to room temperature, and stirred at the same temperature over 16 h. On completion, the reaction is cooled to 0° C., and quenched with 20% aqueous KOH (3.3 mL) and H$_2$O (6.6 mL). The suspension is extracted with DCM (50 mL×2). The organic phases are dried over anhydrous Na$_2$SO$_4$, filtered and concentrated to give 4 (5.0 g crude) as a yellow oil.

Step 4

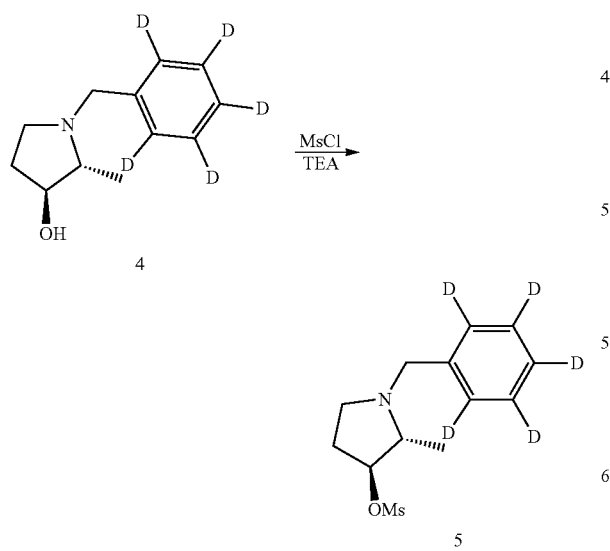

To a stirred solution of 4 (5.0 g, 25.47 mmol) and Et$_3$N (5.15 g, 50.94 mmol) in DCM (50 mL) at 0° C. is added MsCl (4.4 g, 38.21 mmol). The reaction mixture is stirred at r.t for 3 h, then quenched with saturated aqueous NaHCO$_3$ (50 mL×2) and the aqueous layer extracted with DCM (50 mL). The combined organic phase is washed with brine (50 mL). The organic phase is concentrated under reduced pressure to give 5 (6.3 g crude) as a yellow oil.

Step 5

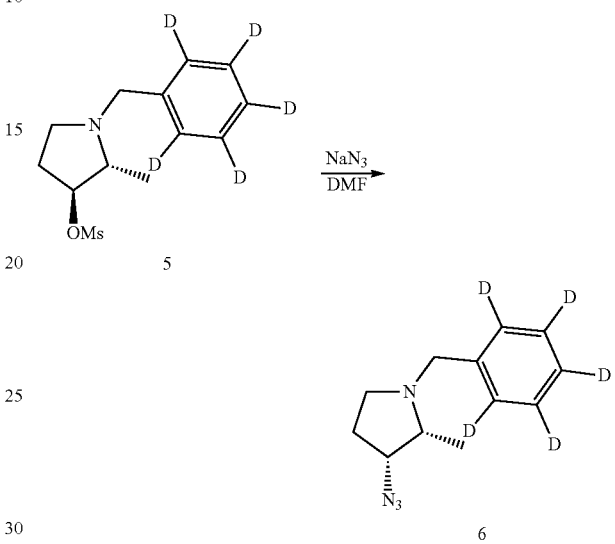

To a stirred solution of 5 (6.3 g, 22.96 mmol) in DMF (63 mL) is added NaN$_3$ (4.5 g, 68.9 mmol) at r.t. The reaction mixture is stirred for 16 h at 80° C. The reaction mixture is quenched with water (100 mL), extracted with EtOAc (70 mL×2). The organic phase is washed with brine (60 mL). The organic phase is concentrated, then MeOH (60 mL×2) is added and concentrated to about 60 mL. The solution of 6 in MeOH is used directly for next step.

Step 6

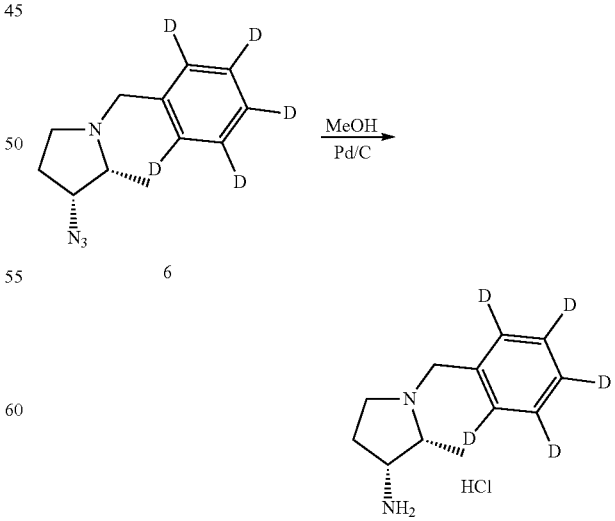

A mixture of 6 and 10% of Pd/C (0.6 g) in MeOH (60 mL) is stirred under H₂ (atmospheric pressure) over 24 h at r.t. The reaction mixture is filtered and the solvent evaporated, and it is diluted with EtOAc (10 mL). HCl (4 mol/L in EtOAc) (6 mL, 24 mmol) is added to the solution. The reaction mixture is stirred at r.t for 1 h, then filtered to give 7 (0.7 g) as a yellow solid.

Step 7

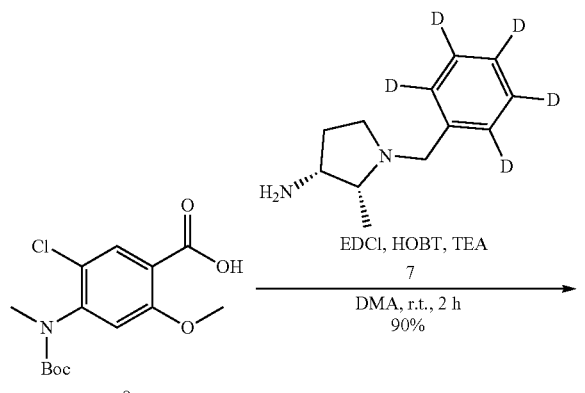

8

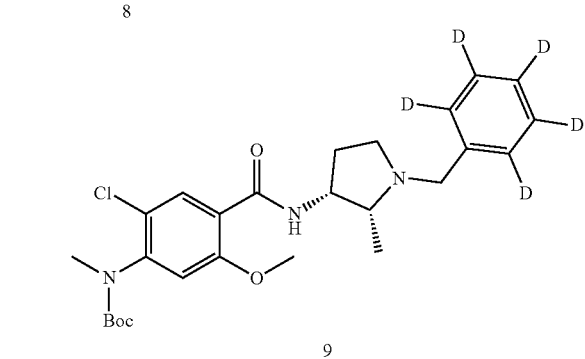

9

To a stirred solution of 8 (500 mg, 1.6 mmol) in Et₃N (320 mg, 3.17 mmol) and DMA (10 mL) is added 7 (371 mg, 1.9 mmol), HOBt (321 mg, 2.4 mmol), and EDCI (454 mg, 2.4 mmol). Mixture is stirred at r.t. for 2 h. The resulting mixture is quenched with water (50 mL) and extracted with EtOAc (50 mL×3), washed with brine (50 mL×1) and dried over anhydrous Na₂SO₄. The organic phase is concentrated to afford 9 (700 mg, 90% yield) as a brown oil.

Step 8

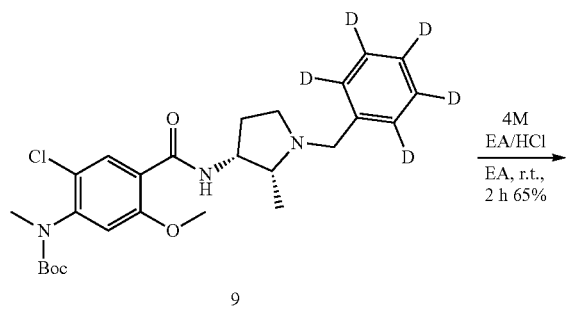

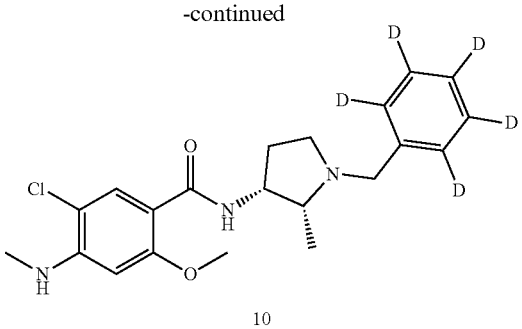

10

A solution of 9 (700 mg, 1.4 mmol) is stirred in HCl (4 mol/L in EtOAc) (10 mL, 40.0 mmol) at r.t. for 2 h. The reaction mixture is concentrated and the residue is diluted with EtOAc (25 mL) and extracted with H₂O (25 mL×2). The aqueous phase is combined and alkalized to pH~11 with sodium hydroxide, extracted with EtOAc (25 mL×3) and the combined organic phase is washed with brine (25 mL×1) and dried over anhydrous Na₂SO₄. The organic phase is concentrated and the residue is purified by column chromatography (silica gel, 40 g; 0-100% EtOAc in hexanes) to afford 10 (370 mg, 65% yield) as an off grey solid. $^1$H NMR (400 MHz, DMSO-d₆) δ 7.93 (d, J=8.8 Hz, 1H), 7.74 (s, 1H), 6.26 (s, 1H), 6.14-6.06 (m, 1H), 4.48-4.37 (m, 1H), 3.98 (s, 3H), 3.95 (s, 1H), 3.18 (d, J=13.2 Hz, 1H), 2.85 (d, J=4.8 Hz, 3H), 2.81-2.79 (m, 1H), 2.64-2.53 (m, 1H), 2.16-2.04 (m, 2H), 1.57-1.48 (m, 1H), 1.00 (d, J=6.3 Hz, 3H). LC-MS (ESI) m/z calcd for $C_{21}H_{21}D_5ClN_3O_2$ (M+H)⁺ 392.9. found 393.3.

Example 2

Synthesis: 5-Chloro-N-((2R,3R)-1-((phenyl)methyl)-2-methylpyrrolidin-3-yl)-2-trideuteromethoxy-4-(methylamino)benzamide

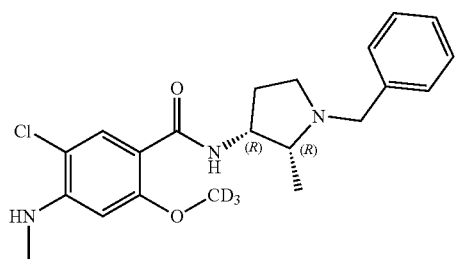

Step 1

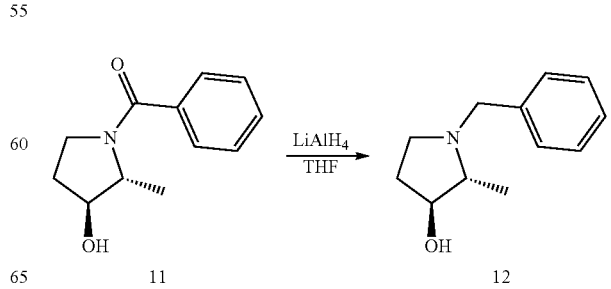

11    12

A solution of 11 (5.0 g, 24.36 mmol) in dry THF (50 mL) is dropwise added to a stirring solution of LiAlH$_4$ (1.58 g, 41.41 mmol) in dry THF (50 mL) at 0~10° C. under nitrogen atmosphere. After stirring at 0~10° C. for 45 min, the reaction is allowed to warm to room temperature, and stirred at the same temperature over 16 h. On completion, the reaction mixture is cooled to 0° C., and quenched with 20% aqueous KOH (2.7 mL) and H$_2$O (5.4 mL). The suspension is extracted with DCM (50 mL×2). The organic phases are dried over anhydrous Na$_2$SO$_4$, filtered and concentrated to give 12 (5.1 g crude, 100% yield) as a yellow oil.

Step 2

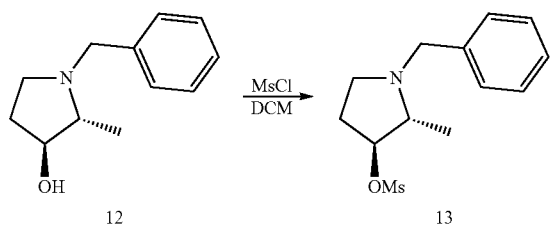

To a stirred solution of 12 (5.1 g, 26.7 mmol) and Et$_3$N (5.4 g, 53.4 mmol) in DCM (51 mL) at 0° C. is added MsCl (3.7 g, 52.3 mmol). The reaction mixture is stirred at r.t for 3 h, then quenched with saturated aqueous NaHCO$_3$ (50 mL×2) and the aqueous layer extracted with DCM (50 mL). The combined organic phase is washed with brine (50 mL). The organic phase is concentrated under reduced pressure to give 13 (7.0 g crude) as a yellow oil.

Step 3

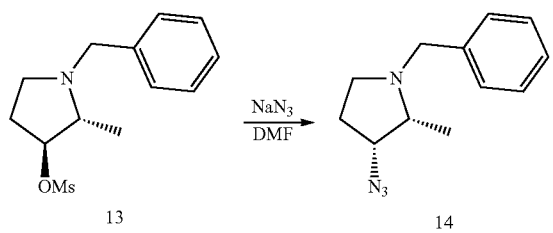

To a stirred solution of 13 (7.0 g, 26 mmol) in DMF (70 mL) is added NaN$_3$ (5.1 g, 78 mmol) at r.t. The reaction mixture is stirred for 16 h at 80° C. It is quenched with water (100 mL) and extracted with EtOAc (70 mL×2). The organic phase is washed with brine (70 mL). The organic phase is concentrated to about 1 L, then MeOH (70 mL×2) is added and concentrated to about 70 mL. The solution of 14 in MeOH is used directly for next step.

Step 4

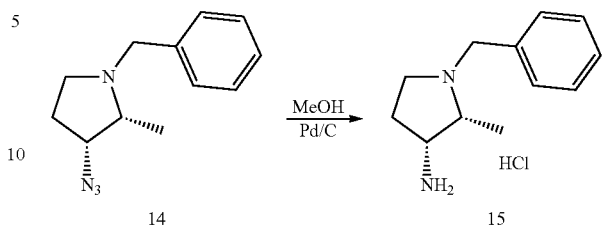

A mixture of 14 and 10% of Pd/C (0.7 g) in MeOH (70 mL) is stirred under H$_2$ (atmospheric pressure) over 24 h at r.t. The reaction mixture is filtered, the solvent evaporated, and then diluted with EtOAc (70 mL). HCl (4 mol/L in EtOAc) (6 mL, 24 mmol) is added to the solution. The reaction mixture is stirred at r.t for 1 h and then filtered to give 15 (1.92 g) as a yellow solid.

Step 5

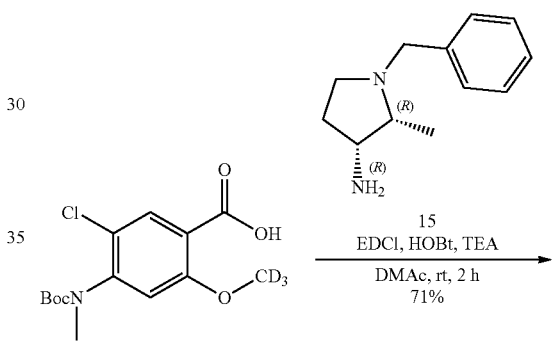

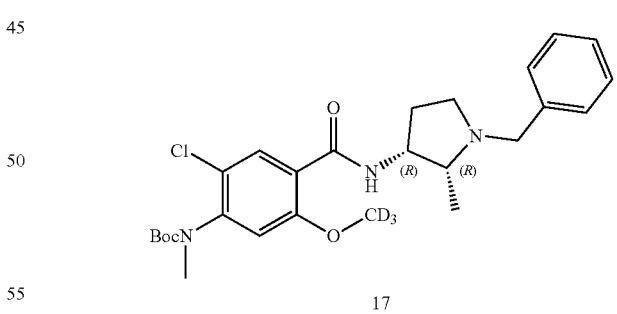

To a stirred solution of 16 (433 mg, 1.3 mmol) in Et$_3$N (274 mg, 2.7 mmol) and DMA (10 mL) is added 15 (308 mg, 1.6 mmol), HOBt (273 mg, 2.0 mmol), and EDCI (387 mg, 2.02 mmol). The reaction mixture is stirred at r.t. for 2 h. The resulting mixture is quenched with water (50 mL) and extracted with EtOAc (50 mL×3), washed with brine (50 mL×1) and dried over anhydrous Na$_2$SO$_4$. The organic phase is concentrated and the residue is purified by column chromatography (silica gel, 40 g; 0-10% methanol in dichloromethane) to afford 17 (450 mg, 71% yield) as a brown oil.

Step 6

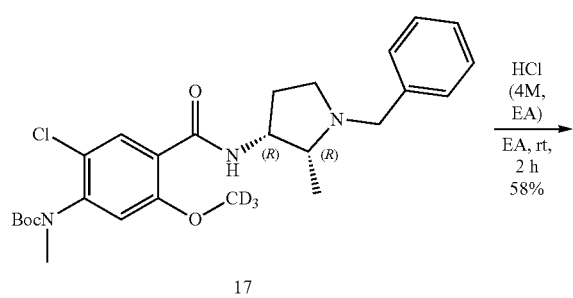

To a stirred solution of 17 (450 mg, 0.9 mmol) is added in HCl (4 mol/L in EtOAc) (10 mL, 40.0 mmol). The reaction mixture is stirred at r.t. for 2 h. The reaction mixture is concentrated and the residue is diluted with EtOAc (25 mL) and extracted with H$_2$O (25 mL×2). The aqueous phase is combined and alkalized to pH~11 with sodium hydroxide, extracted with EtOAc (25 mL×3) and the combined organic phases are washed with brine (25 mL×1) and dried over anhydrous Na$_2$SO$_4$. The organic phase is concentrated and the residue is purified by column chromatography (silica gel, 40 g; 0-100% EtOAc in hexanes) to afford 18 (210 mg, 58% yield) as an off grey solid. $^1$H NMR (400 MHz, DMSO-d$_6$) δ 7.94 (d, J=8.8 Hz, 1H), 7.74 (s, 1H), 7.37-7.29 (m, 4H), 7.27-7.21 (m, 1H), 6.25 (s, 1H), 6.17-6.05 (m, 1H), 4.49-4.35 (m, 1H), 3.96 (d, J=13.2 Hz, 1H), 3.18 (d, J=13.2 Hz, 1H), 2.84 (d, J=4.8 Hz, 3H), 2.83-2.77 (m, 1H), 2.60-2.55 (m, 1H), 2.17-2.06 (m, 2H), 1.56-1.46 (m, 1H), 1.00 (d, J=6.2 Hz, 3H). LC-MS (ESI) m/z calcd for C$_{21}$H$_{23}$D$_3$ClN$_3$O$_2$ (M+H)$^+$ 391.1. found 391.1.

Example 3—Radioligand Binding Competition Activity on Recombinant Human Dopamine and Serotonin Receptors Using Filtration Binding Assays Radioligand binding experiments are conducted with membrane preparations. Receptor accession numbers, cellular background, and reference compounds are listed in Table 1.

TABLE 1

| Receptor | Accession Number | Cell Line | Reference Tracer | Reference Competitor |
|---|---|---|---|---|
| D2S | NP_057658.2 | CHO-K1 | [$^3$H]-Spiperone | Risperidone |
| D3 | AAA73929.1 | CHO-K1 | [$^3$H]-R-(+)-7-OH-DPAT | R-(+)-7-OH-DPAT |
| D4.4 | NP_000788.2 | CHO-K1 | [$^3$H]-Spiperone | Haloperidol |
| 5-HT1A | NP_000515.2 | CHO-K1 | [$^3$H]-8-OH-DPAT | 5-HT |
| 5-HT2A | NP_000612.1 | CHO-K1 | [$^3$H]-DOI | 5-HT |
| human D2L | AAB26819.1 | CHO-K1 | [$^3$H]-Spiperone | Risperidone |

The compounds from Example 1 (10) and Example 2 (18) are tested for radioligand binding competition activity at human D2L, D2S, 5-HT1A, and 5-HT2A receptors and results are provided in Table 2.

TABLE 2

| Measure | D2S | D3 | D4 | 5-HT1A | 5-HT2A | D2L |
|---|---|---|---|---|---|---|
| Nemonapride$^a$ (Ki, nM) | 0.1 | 0.2 | 0.4 | 1.4 | 2.3 | 0.01 |
| Nemonapride$^a$ (IC$_{50}$, nM) | 0.5 | 0.3 | 0.8 | 2.7 | 10 | 0.95 |
| cis (R,R) nemonapride$^b$ (Ki, nM) | 0.2 | 0.5 | 0.8 | 1.4 | 3.3 | 0.02 |
| cis (R,R) nemonapride$^b$ (IC$_{50}$, nM) | 1.0$^c$ (1.26, 0.69) | 0.8$^c$ (0.7, 0.95) | 1.6$^c$ (2.25, 0.9) | 2.8$^c$ (4.7, 0.8) | 14.5$^c$ (19.4, 9.7) | 0.2 |
| Ex. 1 (10) (Ki, nM) | 0.13$^c$ (0.05, 0.21) | 1.5 | 1.01 | 0.6$^c$ (0.6, 0.5) | 9.4$^c$ (11.0, 7.7) | 0.04$^c$ (0.02, 0.05) |
| Ex. 1 (10) (IC$_{50}$, nM) | 0.7$^c$ (0.3, 1.1) | 2.8 | 2.0 | 1.2$^c$ (1.2, 1.2) | 24.1 (14.0, 34.1) | 0.3 (0.1, 0.4) |
| Ex. 2 (18) (Ki, nM) | 0.07 | — | — | 0.6 | 9.9 | 0.02 |
| Ex. 2 (18) (IC$_{50}$, nM) | 0.4 | — | — | 1.3 | 12.5 | 0.02 |
| Ex. 1 (A2)$^d$ from International Publication No. WO 2023/130117 (Ki, nM) | 0.2 | 0.5 | 0.7 | 0.5 | 7.4 | 0.02 |

TABLE 2-continued

| | Binding | | | | | |
|---|---|---|---|---|---|---|
| Measure | D2S | D3 | D4 | 5-HT1A | 5-HT2A | D2L |
| Ex. 1 (A2)[d] from International Publication No. WO 2023/130117 (IC$_{50}$, nM) | 1.0[c] (1.25, 0.69) | 0.8[c] (0.82, 0.85) | 1.3[c] (2.06, 0.59) | 1[c] (1.09, 0.91) | 32.9[c] (45.2, 20.5) | 0.2 |

[a](±)-cis-N-(1-Benzyl-2-methylpyrrolidin-3-yl)-5-chloro-2-methoxy-4-methylaminobenzamide
[b]N-[(2R,3R)-1-benzyl-2-methylpyrrolidin-3-yl]-5-chloro-2-methoxy-4-(methylamino)benzamide
[c]Average of numbers in parentheses.
[d]

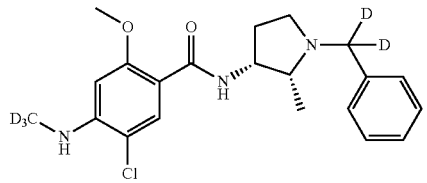

Example 4—Agonist or Antagonist Activity on Recombinant Human Dopamine and Serotonin Receptors Using IPOne HTRF and cAMP HTRF Assays SPA $^{35}$S-GTPgS experiments are conducted with membrane preparations. IP-One and cAMP HTRF assays are conducted with recombinant cell lines. Receptor accession numbers, cellular background, and reference compounds are listed in Table 3.

TABLE 3

| Receptor | Accession Number | Assay | Cell Line | Reference Agonist | Reference Antagonist |
|---|---|---|---|---|---|
| D2S | NP_057658.2 | cAMP | CHO-K1 | Quinpirole | Haloperidol |
| D3 | AAA73929.1 | GTP | CHO-K1 | Dopamine | GR103691 |
| D4.4 | NP_000788.2 | cAMP | CHO-K1 | Dopamine | Spiperone |
| 5-HT1A | NP_000515.2 | cAMP | CHO-K1 | 5-CT | Not tested |
| 5-HT2A | NP_000612.1 | IPOne | CHO-K1 | α-Me-5-HT | Not tested |
| D2L | AAB26819.1 | cAMP | CHO-K1 | Quinpirole | Haloperidol |

The compounds from Example 1 (10) and Example 2 (18) are tested for antagonist activity at human D2L, D2S, D3, and D4.4 receptors and for agonist activity at human 5-HT1A and 5-HT2A receptors. Results are in Tables 4-6.

Agonist activity of test compounds is expressed as a percentage of the activity of the reference agonist at its EC$_{100}$ concentration. Antagonist activity of the test compound is expressed as a percentage of the inhibition of reference agonist activity at its EC$_{80}$ concentration.

TABLE 4

| | Functional Assays | | | | | |
|---|---|---|---|---|---|---|
| Measure (IC$_{50}$, nM) | D2S (antagonist mode) | D2L (antagonist mode) | D3 (antagonist mode) | D4 (antagonist mode) | 5-HT1A (agonist mode) EC$_{50}$ | 5-HT2A (agonist mode) EC$_{50}$ |
| Nemonapride[a] | cAMP 0.3 | cAMP 0.08 | GTPγS 3.0 | cAMP 0.9 | cAMP 14.3 | IP-one 5.5 |
| cis (R,R) nemonapride[b] | cAMP 0.4[c] (0.61, 0.27) | cAMP 0.08 | GTPγS 2.9[c] (1.3, 4.5) | cAMP 1.2[c] (1.41, 0.9) | cAMP 33.5[c] (30, 37.1) | IP-one 3.4[c] (4.4, 2.9, 4.8, 1.6) |
| Ex. 1 (10) | cAMP 0.5[c] (0.48, 0.49) | cAMP 0.5[c] (0.56, 0.35) | — | cAMP 8.6 | cAMP 19.6[c] (18.2, 20.9) | IP-one 5[c] (4.8, 5.2) |
| Ex. 2 (18) | cAMP 0.40 | cAMP 0.42 | — | — | cAMP 20.6 | IP-one 4.4 |
| Ex. 1 (A2) from International Publication No. WO 2023/130117 (see structure above) | cAMP 0.8[c] (1.38, 0.3) | cAMP 0.08 | GTPγS 3.8[c] (3.03, 4.6) | cAMP 2.5[c] (4.67, 0.37) | cAMP 16.1[c] (19.8, 12.3) | IP-one 4.9[c] (4.3, 1.5, 9.1, 4.9) |

[a](±)-cis-N-(1-Benzyl-2-methylpyrrolidin-3-yl)-5-chloro-2-methoxy-4-methylaminobenzamide
[b]N-[(2R,3R)-1-benzyl-2-methylpyrrolidin-3-yl]-5-chloro-2-methoxy-4-(methylamino)benzamide
[c]Average of numbers in parentheses.

TABLE 5

| Measure[a] | D2S (antagonist mode) | D2L (antagonist mode) | D3 (antagonist mode) | D4 (antagonist mode) | 5-HT1A (agonist mode) | 5-HT2A (agonist mode) |
|---|---|---|---|---|---|---|
| Nemonapride[b] | cAMP 97 | cAMP 86 | GTPγS 126 | cAMP 75 | cAMP 52 | IP-one 48 |
| cis (R,R) nemonapride[c] | cAMP 99[d] (105, 92) | cAMP 94 | GTPγS 99[d] (80, 118) | cAMP 111[d] (117, 105) | cAMP 78[d] (93, 62) | IP-one 44[d] (25, 57, 31, 63) |
| Ex. 1 (10) | cAMP 100[d] (102, 98) | cAMP 103[d] (100, 106) | — | cAMP 92 | cAMP 71[d] (64, 78) | IP-one 84[d] (91, 76) |
| Ex. 2 (18) | cAMP 103 | cAMP 97 | — | — | cAMP 59 | IP-one 94 |
| Ex. 1 (A2) from International Publication No. WO 2023/130117 (see structure above) | cAMP 99[d] (104, 93) | cAMP 81 | GTPγS 122[d] (130, 115) | cAMP 100[d] (111, 89) | cAMP 64[d] (65, 62) | IP-one 69[d] (53, 82, 68, 72) |

[a]Top % Inhibition or Activation at maximal concentration
[b](±)-cis-N-(1-Benzyl-2-methylpyrrolidin-3-yl)-5-chloro-2-methoxy-4-methylaminobenzamide
[c]N-[(2R,3R)-1-benzyl-2-methylpyrrolidin-3-yl]-5-chloro-2-methoxy-4-(methylamino)benzamide
[d]Average of numbers in parentheses.

As shown above, the deuterated compounds of Examples 1 (10) and 2 (18) are D2 antagonists and 5-HT2A agonists. The deuterated compound of Example 1 (10) is a strong 5-HT1A agonist. The deuterated compound of Example 2 (18) is a 5-HT1A partial agonist.

TABLE 6

| Ratio with 5-HT2A activity | 5-HT2A:D2L |
|---|---|
| cis (R,R) nemonapride[a] | 43 |
| Ex. 1 (10) | 10 |
| Ex. 2 (18) | 11 |
| Ex. 1 (A2) from International Publication No. WO 2023/130117 (see structure above) | 61 |

[a]N-[(2R,3R)-1-benzyl-2-methylpyrrolidin-3-yl]-5-chloro-2-methoxy-4-(methylamino)benzamide Example 5—In Vivo Pharmacokinetics Group A male Sprague-Dawley (SD) rats are dosed (by PO) with test compounds at 0.5 mg/kg and 5 mg/kg (N=3 animals/dose level). Blood samples are obtained at 5, 10, and 30 minutes and 1, 2, 4, 8, and 24 hours after dosing. Following blood collection at 24 hours, brain perfusion is performed on the animals before harvesting brain tissues.

Group B male Sprague-Dawley (SD) rats are dosed (by PO) with test compounds at 0.5 mg/kg and 5 mg/kg (N=9 animals/dose level). At designated timepoints (1, 4, and 8 hours), three animals from each dose group undergo blood draw followed by brain perfusion before samples are collected.

Test compounds are the deuterated compounds of Example 1 (10) and Example 2 (18) and N-[(2R,3R)-1-benzyl-2-methylpyrrolidin-3-yl]-5-chloro-2-methoxy-4-(methylamino)benzamide (cis (R,R) nemonapride).

Rats are surgically cannulated with femoral artery catheter for blood collection. Approximate weight of rats is 250-350 g. Water is provided ad libitum. Fasting overnight prior to oral dose. Food available 4 h post dose.

Dose formulations are 0.5% aqueous methylcellulose (4000 cps) with 0.1% Tween™ 80 for PO administration. Once prepared, the suspension is vortexed/homogenized and continuously stirred until administration. Dose concentration: 0.1 mg/mL for 0.5 mg/kg dose and 1 mg/mL for 5 mg/kg dose. Route of administration: oral gavage. Dose volume: 5 mL/kg.

Blood samples are obtained via an automated sampling system in tubes containing potassium EDTA anticoagulant up to 24 h post dose. Plasma is obtained by centrifugation and snap frozen on dry ice within 30 minutes after collection. Aliquots of each dose formulation are taken, diluted appropriately, and analyzed at the same time with plasma samples by LC-MS/MS.

Plasma (harvested from blood samples) and brain tissues (homogenized and processed) are analyzed by LC/MS/MS. Plasma is harvested from blood via centrifugation within 30 minutes of sample collection. Brain tissue is collected after animals undergo perfusion to remove residual cardiovascular blood.

Dose solutions, plasma (harvested from blood), and brain tissues (homogenized and processed) are stored at −20° C. until analysis.

Plasma samples are thawed at room temperature before adding an organic solvent containing an internal standard to precipitate proteins.

Brain samples are thawed and homogenized in water (3-4 volumes) and aliquots of homogenates analyzed by LC/MS/MS.

Results are shown in FIGS. 1-6.

Figure 3:
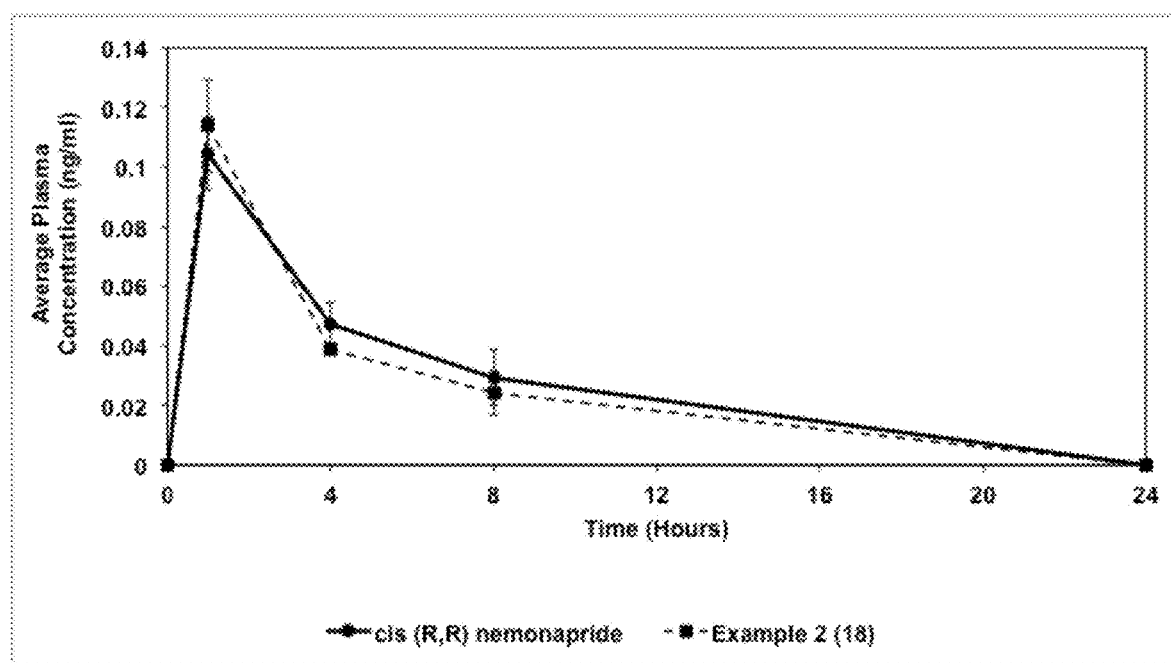
FIG. 3 shows average plasma concentration (ng/ml) in rats of cis (R,R) nemonapride and the compound of Example 2 (18) when administered at a single PO dose of 0.5 mg/kg.

Plasma pharmacokinetics between N-[(2R,3R)-1-benzyl-2-methylpyrrolidin-3-yl]-5-chloro-2-methoxy-4-(methylamino)benzamide (cis (R,R) nemonapride) and the deuterated compounds of Example 1 (10) and Example 2 (18) are similar (see FIG. 1, see also FIG. 3). In FIGS. 1 and 3, cis (R,R) nemonapride data is shown as the solid line and data for the deuterated compounds of Example 1 (10) and Example 2 (18) are shown as the dashed line.

Figure 5:
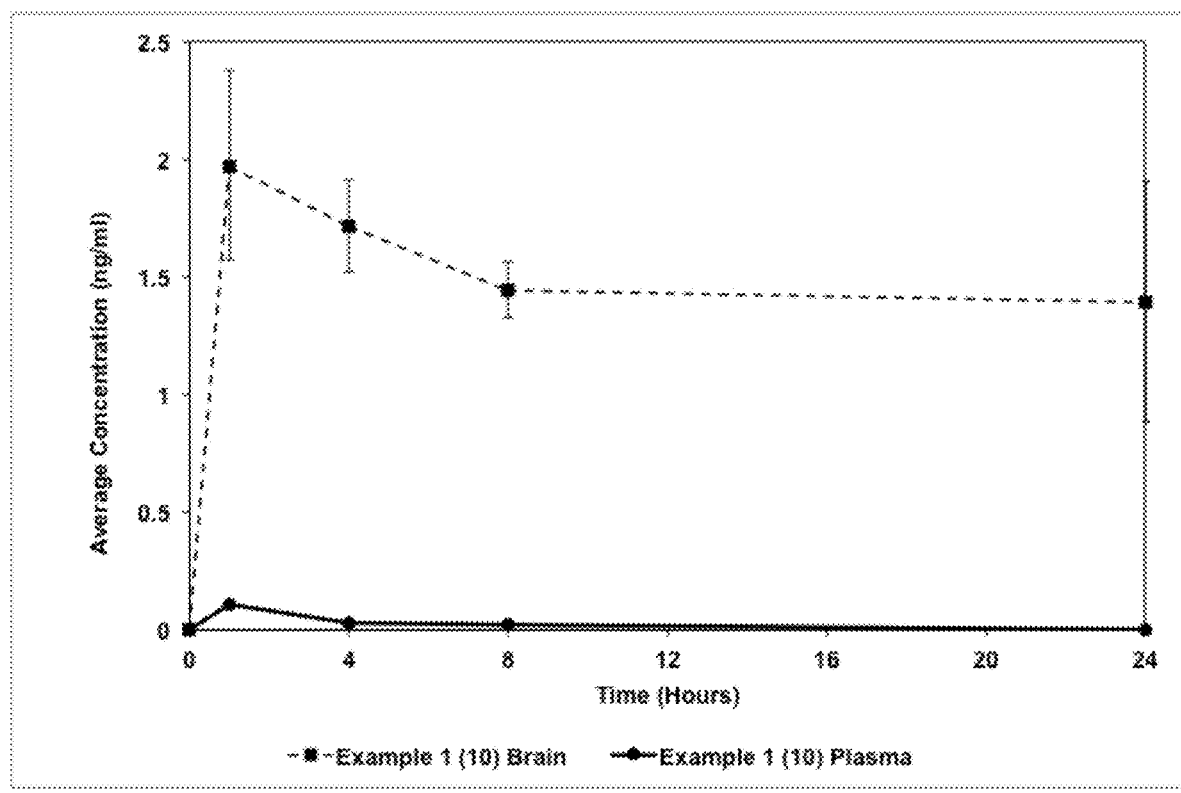
FIG. 5 shows average plasma and brain concentrations (ng/ml) in rats of the compound of Example 1 (10) when administered at a single PO dose of 0.5 mg/kg.
Figure 6:
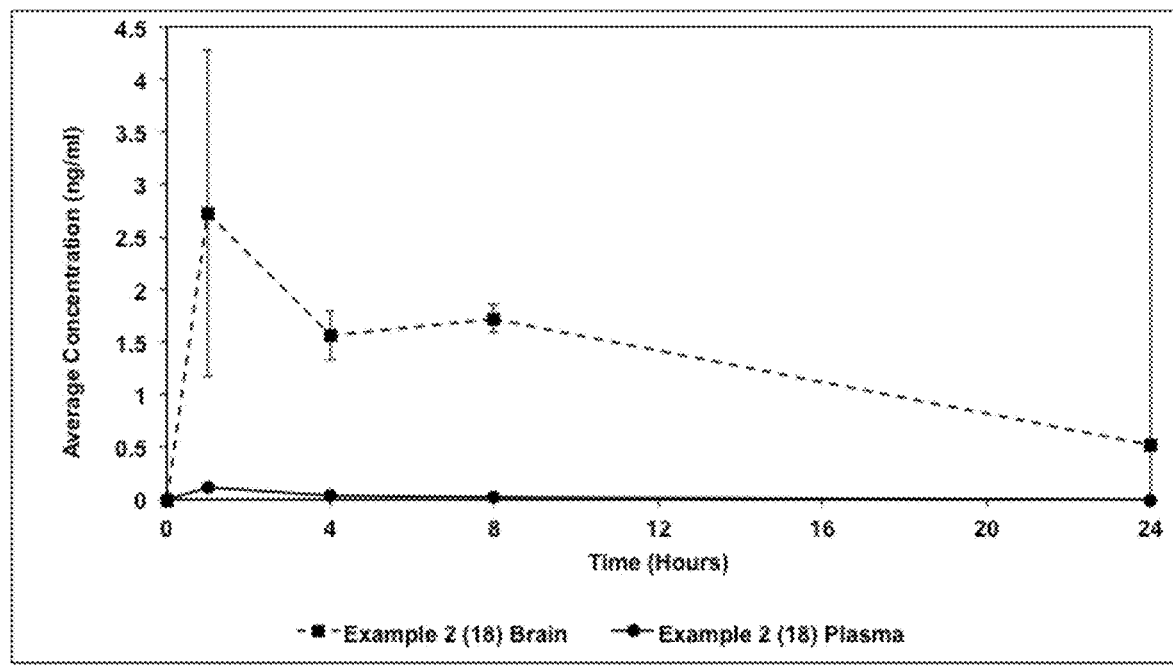
FIG. 6 shows average plasma and brain concentrations (ng/ml) in rats of the compound of Example 2 (18) when administered at a single PO dose of 0.5 mg/kg.

The extended brain enrichment of the deuterated compounds of Example 1 (10) and Example 2 (18) in rats following a single PO dose of 0.5 mg/kg are shown in FIGS. 5 and 6, respectively. In each figure, average brain concentration (ng/ml) is shown as the dashed line and average plasma concentration (ng/ml) is shown as the solid line.

The deuterated compounds of Example 1 (10) and Example 2 (18) have enriched brain levels compared to N-[(2R,3R)-1-benzyl-2-methylpyrrolidin-3-yl]-5-chloro-2-methoxy-4-(methylamino)benzamide (cis (R,R) nemonapride) (see FIGS. 2 and 4, all are administered at a single PO dose of 0.5 mg/kg). A comparison of brain to plasma ratios for N-[(2R,3R)-1-benzyl-2-methylpyrrolidin-3-yl]-5-chloro-2-methoxy-4-(methylamino)benzamide (cis (R,R) nemonapride) and the deuterated compounds of Example 1 (10) and Example 2 (18) are in Table 7 (all are administered at a single PO dose of 0.5 mg/kg).

TABLE 7

| Time (hours) | cis (R,R) nemonapride Average Brain to Plasma Partitioning | Compound from Example 1 (10) Average Brain to Plasma Partitioning | Compound from Example 2 (18) Average Brain to Plasma Partitioning |
|---|---|---|---|
| 1 | 6 | 18 | 22 |
| 4 | 17 | 65 | 41 |
| 8 | 33 | 75 | 91 |
| 24 | ND (plasma values below quantitation limit) | 85 | 43 |

TABLE 8

Plasma Concentrations (ng/ml) versus Time

|  | Example 1 (10) | Example 2 (18) | Example 1 (10) | Example 2 (18) |
|---|---|---|---|---|
| Dose (mg/kg) | 0.5 | 0.5 | 5 | 5 |
| Cmax (ng/ml) | 0.32 | 0.11 | 1.90 | 1.24 |
| Tmax (h) | 0.14 | 0.36 | 0.14 | 0.42 |
| AUC (ng-h/ml) | 0.65 | 0.24 | 4.42 | 3.70 |

TABLE 9

Brain Concentrations (ng/ml) versus Time

|  | Example 1 (10) | Example 2 (18) | Example 1 (10) | Example 2 (18) |
|---|---|---|---|---|
| Dose (mg/kg) | 0.5 | 0.5 | 5 | 5 |
| Cmax (ng/ml) | 1.97 | 2.72 | 9.64 | 9.64 |
| Tmax (h) | 1 | 1 | 2 | 1 |
| AUC (ng-h/ml) | 35.53 | 32.24 | 116.53 | 128.09 |
| Brain/Plasma Ratio | 54 | 133 | 26 | 35 |

Example 6—Ex Vivo Radioligand Binding in Membrane Preparations to Determine Time-Course of Receptor Occupancy at Central $D_2$ Receptors This study is to determine receptor occupancy at central D2 receptors following oral administration of the deuterated compound of Example 1 (10) or Example 2 (18) at various time points (e.g., 1, 2, 4, 8, and 24 hours) and the positive comparator, olanzapine (10 mg/kg, po) using [$^3$H]raclopride and rat striatal membranes. Liquid scintillation counting is used to quantify radioactivity.
Animals
Rats.
Drug Treatment
On day of test, animals are dosed orally with either vehicle, a single dose of the deuterated compound of Example 1 (10) or Example 2 (18), or olanzapine. Rats are sacrificed at specified time points, e.g., 1, 2, 4, 8, and 24 hours after drug administration or 1 hour after vehicle and olanzapine administration.
Pharmacokinetics
A post-mortem blood sample is taken by cardiac puncture. Plasma is taken for PK determination.
Whole brains are removed, rinsed with saline, and blot dried. The left striatum and right striatum is dissected out and weighed before being frozen on dry ice.
Homogenate Preparation
The striata is homogenised individually.
Assay
Striatal homogenates are incubated with [$^3$H]raclopride. Radioactivity is determined by liquid scintillation counting.

Example 7—Touchscreen-Based Rat Probabilistic Reward Task

The Probabilistic Reward Task (PRT) uses visual discrimination methodology to quantify reward responsiveness to both identify deficits and characterize drug-induced improvements. Groups of rats are trained on the touchscreen-based PRT and exposed to asymmetrical probabilistic contingencies to generate response biases to the richly rewarded stimulus (Pizzagalli, D. et al., Biological Psychiatry, 2005, 57, 319-327; Kangas, B. et al., Translational Psychiatry, 2020, 10 (1): 285; Wooldridge, L. et al., International Journal of Neuropsychopharmacology, 2021, 24, 409-418). Next, subjects are tested with vehicle or the deuterated compound of Example 1 (10) or Example 2 (18)).
Details and schematics of the rodent touch-sensitive experimental chamber and methods can be found in Kangas, B. et al., Behavioural Pharmacology, 2017, 28, 623-629.

Example 8—Conditioned Avoidance Response

Rats are used. Risperidone (0.5 mg/kg; Sigma Aldrich) is dissolved in 10% DMSO in water and injected i.p. at a dose volume of 1 mg/kg 30 minutes prior to test. The deuterated compound of Example 1 (10) or Example 2 (18) is administered orally prior to test.
The Conditioned Avoidance Response (CAR) Test is an animal model screening for antipsychotic drugs.

Example 9—Headshake Response

Rats are used. The deuterated compound of Example 1 (10) or Example 2 (18) is administered orally.
Animals are administered vehicle, DOI, or test compound and returned to their holding cage for the appropriate pretreatment time, following which headshakes are recorded. The headshake response is a rapid, rhythmic shaking of the head in a radial motion. Data are analyzed by ANOVA followed by post hoc analysis where appropriate.

Example 10—DOI-Induced Headshake Response

Rats are used. The deuterated compound of Example 1 (10) or Example 2 (18) is administered orally. DOI is administered IP. Ketanserin (1 mg/kg) is injected IP.
Animals are administered vehicle, ketanserin, or test compound and returned to their holding cage for the appropriate pretreatment time. Rats are then injected with DOI and headshakes are recorded 10 minutes after DOI injection for 10 minutes. The headshake response is a rapid, rhythmic shaking of the head in a radial motion. Data is analyzed by ANOVA followed by post hoc analysis where appropriate.

Example 11—Synthesis of Starting Materials for Examples 1 and 2

Intermediate 15: tert-butyl (R)-2-methyl-3,5-dioxopyrrolidine-1-carboxylate

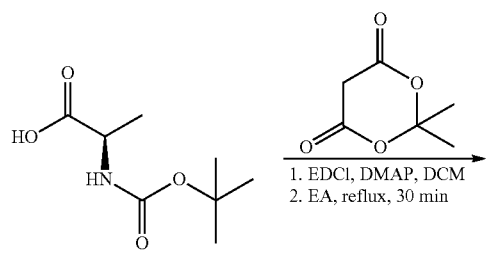

To a stirred solution of Boc-D-alanine (500 g, 2.64 mol), Meldrum's acid (400 g, 2.78 mol) and DMAP (388 g, 3.18 mol) in CH$_2$Cl$_2$ (5 L) is added EDCI (608 g, 3.18 mol) under nitrogen at 0° C. The resulting solution is then allowed to warm up to room temperature (rt) and stirred over 16 h. It is quenched with water (1.5 L), the organic phase is washed with a cold solution of 5% KHSO$_4$ (3 L×3), water (3 L×1), and brine, then dried over anhydrous MgSO$_4$, and concentrated to give the residue. EtOAc (4 L) is added and the reaction mixture is refluxed for 2 hours. The solution is concentrated and the residue is stirred in EtOAc (500 ml) at −15° C. for 2 h, then filtered, and the filter cake is collected to give the title compound as a white solid (150 g, 27% yield). The mother liquid is further refluxed for 2 hours then stirred in EA at −10° C. and filtered to give the title compound (40 g) as a white solid. $^1$H NMR (400 MHz, CDCl$_3$) δ 4.45 (q, J=6.8 Hz, 1H), 3.22 (s, 2H), 1.57 (s, 9H), 1.51 (d, J=6.8 Hz, 3H). MS m/z (ESI): 158 [M+H−56]$^+$ Intermediate 16: tert-butyl (2R,3R)-3-hydroxy-2-methyl-5-oxopyrrolidine-1-carboxylate

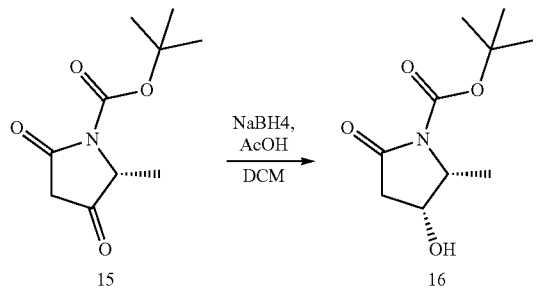

To a stirred solution of compound 15 (40 g, 187.6 mmol) in DCM (400 ml) is added AcOH (200 mL) at 0° C., then NaBH$_4$ (21.3 g, 562.8 mmol) is added in three portions. The resulting solution is then allowed to warm up to room temperature and stirred over 16 h. The reaction mixture is quenched with 5% NaHCO$_3$ at 0° C. It is extracted with DCM (200 mL×3). The combined organic layer is washed with 5% NaHCO$_3$ solution. The organic phase is dried over anhydrous MgSO$_4$ and concentrated to give the residue that is stirred in isopropyl ether and filtered to give the title compound 16 (24 g, 59.4% yield). $^1$H NMR (400 MHz, CDCl$_3$) δ 4.53-4.47 (m, 1H), 4.29-4.22 (m, 1H), 2.75-2.55 (m, 2H), 1.53 (s, 9H), 1.31 (d, J=6.8 Hz, 3H). MS m/z (ESI): 160 [M+H−56]$^+$ Intermediate 17: tert-butyl (2R,3R)-3-hydroxy-2-methylpyrrolidine-1-carboxylate

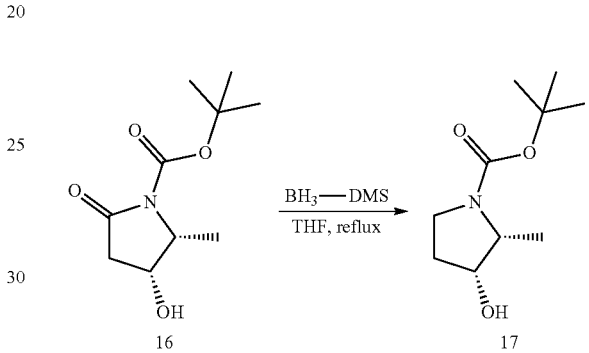

To a solution of compound 16 (87 g, 405 mmol) in dry THF (1 L) is added a solution of BH$_3$—SMe$_2$ (600 mL, 1200 mmol) at 0° C. and it is stirred for 30 min at 0° C. Then the mixture is refluxed for 4 h. The resulting mixture is cooled and quenched with saturated NH$_4$Cl at 0° C. It is then extracted with EtOAc (1 L×3). The organic phases are dried over anhydrous MgSO$_4$ and concentrated to give compound 17 (70 g, 86% yield). $^1$H NMR (400 MHz, DMSO-d$_6$) δ 5.11 (s, 1H), 4.19-4.10 (m, 1H), 3.83-3.63 (m, 1H), 3.22-2.89 (m, 2H), 1.87-1.54 (m, 2H), 1.38 (s, 9H), 0.85 (d, J=6.8 Hz, 3H). MS m/z (ESI): 146 [M+H−56]$^+$ Intermediate 18 (Intermediate Used for Synthesis)

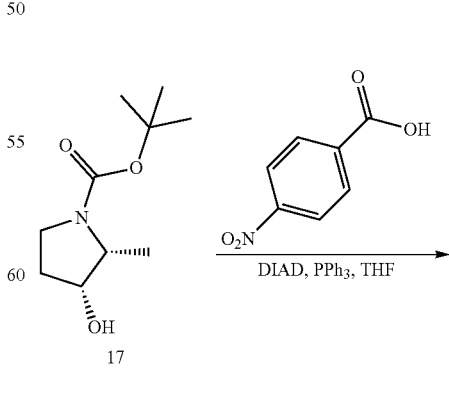

To a cold solution of compound 17 (15.74 g, 78.2 mmol), 4-nitrobenzoic acid (13.72 g, 82.1 mmol), and PPh$_3$ (16.42 g, 62.6 mmol) in dry THF (250 ml) is added DIAD (16.6 g, 82.1 mmol). The reaction mixture is stirred for 30 minutes at 0° C. The reaction mixture is allowed to warm room temperature for 16 h. The resulting mixture is cooled and quenched with water. The mixture is extracted with EtOAc (200 ml×3), dried over anhydrous MgSO$_4$, and then concentrated. The residue is purified by silica gel chromatography to afford intermediate 18 (24.7 g, 90.1% yield). $^1$H NMR (400 MHz, CDCl$_3$) δ 8.31-8.17 (m, 4H), 5.20 (d, J=4 Hz, 1H), 4.17-3.86 (m, 1H), 3.59-3.46 (m, 2H), 2.35-2.11 (m, 2H) 1.48 (s, 9H), 1.28 (d, J=6.8 Hz, 3H). MS m/z (ESI): 295 [M+H−56]$^+$ Intermediate 19: (2R,3S)-2-methylpyrrolidin-3-yl 4-nitrobenzoate A mixture of intermediate 18 (23.4 g, 66.8 mmol) and TFA (120 mL) in DCM (240 mL) is stirred at room temperature for 1 and then it is concentrated to give compound 19 (16.7 g, 100% yield). LCMS: M+1=251

Intermediate 20: (2R,3S)-1-benzoyl-2-methylpyrrolidin-3-yl 4-nitrobenzoate

To a solution of compound 19 (16.7 g, 66.8 mmol) in toluene (520 ml) is added 2N NaOH (520 ml, 104 mmol), then benzoyl chloride (9.6 g, 66.8 mmol) in toluene (200 ml) is added at 0° C. The mixture is separated and the aqueous phase is extracted with DCM (250 ml×3). The combined organic phase is dried over MgSO$_4$ and concentrated to give compound 20 (21.3 g, 90% yield). LCMS: M+1=355

Intermediate 21: ((2R,3S)-3-hydroxy-2-methylpyrrolidin-1-yl) (phenyl) methanone

To a stirred solution of compound 20 (21.3 g, 60.1 mmol) in MeOH (400 mL) is added 6N NaOH (11 ml, 66 mmol). The reaction mixture is stirred for 40 minutes and concentrated under reduced pressure. The residue is diluted with DCM (200 ml) and water (100 ml). The aqueous phase is extracted with DCM (250 ml×3). The organic phase is dried over MgSO$_4$ and concentrated to give the residue that is treated with petroleum ether (10 ml) and EtOAc (2 ml) to afford intermediate 21 (9.85 g, 79.8% yield). LCMS: M+1=206

Example 12—Synthesis of Starting Material for Example 1

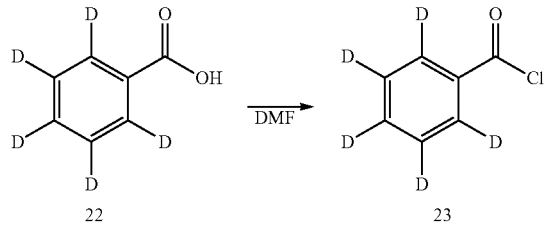

22 (7.5 g, 59 mmol) is dissolved in cold DCM (200 mL, 0° C.). To the solution is added 3 drops of DMF and oxalyl chloride (118 mmol, dropwise). The reaction is allowed to warm to room temperature and is stirred for 3 hours. The solvent is removed under reduced pressure to yield 23 (100% yield, 8.59 g).

Example 13—Microdialysis

For microdialysis experiments, male rats (n=8/experimental session) are surgically implanted with probes in the nucleus accumbens and prefrontal cortex. Rats are given a recovery period of at least 16 hours. During this time the probes are continuously perfused with an artificial cerebrospinal fluid.

Microdialysate samples are collected from freely moving rats at 30 minute intervals for a baseline period of 2 hours prior to test compound/vehicle administration. Samples are collected for 8 hours post test compound/vehicle administration.

Test compounds are the compound of Example 1 (10) and the compound from Example 1 (A2) of International Publication No. WO 2023/130117.

Test compounds are administered 2.5 mg/kg in 0.5% methylcellulose (po, oral gavage)+saline (ip). Vehicle is 0.5% methylcellulose (po, oral gavage)+saline (ip).

Detection and subsequent quantification of neurotransmitter in the samples is based on HPLC coupled with electrochemical detection. Data are log transformed and statistical comparisons are made using the Williams' test and multiple t-tests.

Microdialysis data are log transformed. Baseline is defined as the geometric mean of the four pre-treatment samples (those collected at −90, −60, −30, and 0 minutes). To address extreme values, analysis is performed by robust regression using M estimation, Huber weighting, using a default parameter with treatment as a factor and log (baseline) as a covariate.

Data from the prefrontal cortex of one rat is excluded due to decreasing levels throughout the experiment. Data from the nucleus accumbens of one rat is not obtained. Dopamine levels from two rats are excluded due to outlying values.

Each time point is analyzed separately, or in bins and overall (0-2, 0-4, 0-8 hours after dosing). For calculation of hourly and 2 hourly means, any missing data is imputed to be the geometric mean of the previous and subsequent values. Comparisons to vehicle are by Williams' test or multiple t tests for comparisons across groups.

The compound of Example 1 (10) transiently decreases (to 1.5 hours) 5-HT in the nucleus accumbens and does not significantly alter 5-HT levels in the pre-frontal cortex.

Figure 7:
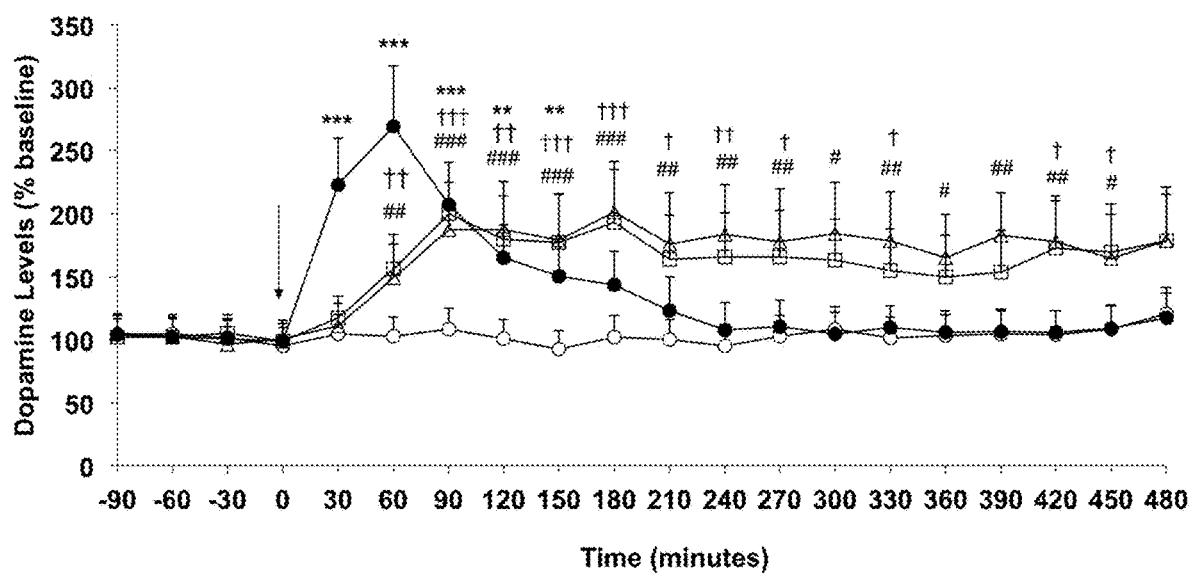
FIG. 7 shows effects of administration of Example 1 (10) and Example 1 (A2) from International Publication No. WO 2023/130117 on dopamine in the nucleus accumbens of freely-moving Sprague Dawley rats (% baseline).
Figure 8:
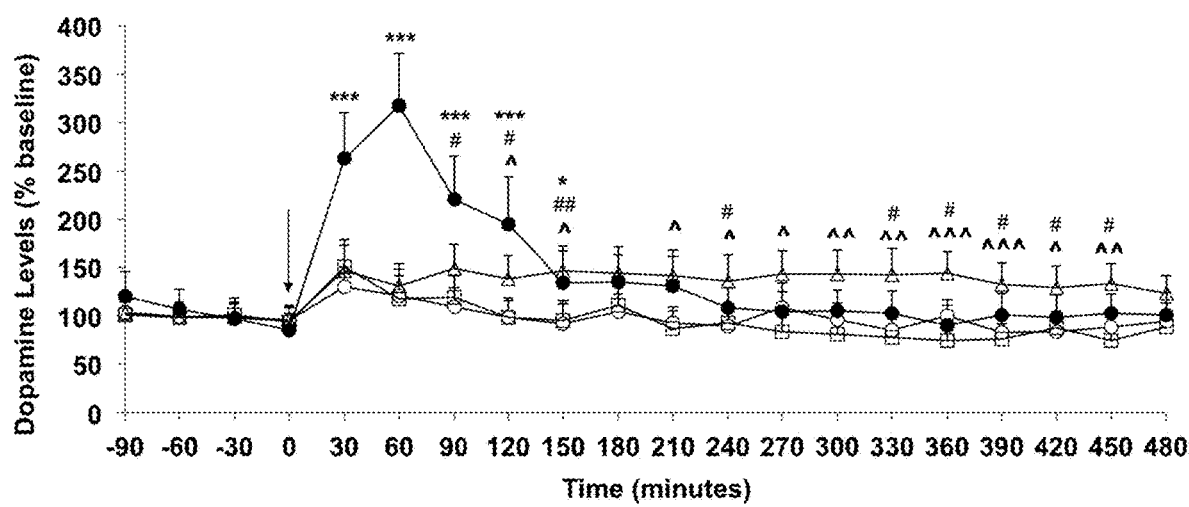
FIG. 8 shows effects of administration of Example 1 (10) and Example 1 (A2) from International Publication No. WO 2023/130117 on dopamine in the prefrontal cortex of freely-moving Sprague Dawley rats (% baseline).

Results for dopamine are show in FIGS. 7 and 8.

In FIG. 7, the open circles are 0.5% methylcellulose (5 ml/kg po)+saline (2 ml/kg ip), the filled circles are 0.5% methylcellulose (5 ml/kg po)+d-amphetamine (0.3 mg/kg ip), the open squares are Example 1 (A2) from International Publication No. WO 2023/130117 (2.5 mg/kg po)+saline (ip), and the open triangles are the compound from Example 1 (10) (2.5 mg/kg po)+saline (ip).

In FIG. 7, results are adjusted means; n=6-8. SEMs are calculated from the residuals of the statistical model. Drug doses are for the free base and vertical arrow indicates time of drug administration. Data are log-transformed and analysed by robust regression with log (baseline) as a covariate. A2 is compared to vehicle by Williams' test. Other comparisons to vehicle are by the multiple t test. 10 is compared to A2 by multiple t test.

In FIG. 7, significant differences of 0.5% methylcellulose (5 ml/kg po)+d-amphetamine vs vehicle: *$p<0.05$, $p<0.01$, *$p<0.001$. Significant differences of A2 vs vehicle: †$p<0.05$, ††$p<0.01$, †††$p<0.001$. Significant differences of 10 vs vehicle: #$p<0.05$, ##$p<0.01$, ###$p<0.001$.

As shown in FIG. 7, the compound of Example 1 (10) shows a significant and sustained (most of the 8-hour test duration) increase of dopamine in the nucleus accumbens. Effect is similar as the deuterated compound of Example 1 (A2) from International Publication No. WO 2023/130117.

In FIG. 8, the open circles are 0.5% methylcellulose (5 ml/kg po)+saline (2 ml/kg ip), the filled circles are 0.5% methylcellulose (5 ml/kg po)+d-amphetamine (0.3 mg/kg ip), the open squares are Example 1 (A2) from International Publication No. WO 2023/130117 (2.5 mg/kg po)+saline (ip), and the open triangles are the compound from Example 1 (10) (2.5 mg/kg po)+saline (ip).

In FIG. 8, results are adjusted means; n=7-8. SEMs are calculated from the residuals of the statistical model. Drug doses are for the free base and vertical arrow indicates time of drug administration. Data are log-transformed and analysed by robust regression with log (baseline) as a covariate. A2 is compared to vehicle by Williams' test. Other comparisons to vehicle are by the multiple t test. 10 is compared to A2 by multiple t test.

In FIG. 8, significant differences of 0.5% methylcellulose (5 ml/kg po)+d-amphetamine vs vehicle: *$p<0.05$, $p<0.01$, *$p<0.001$. Significant differences of 10 vs vehicle: #$p<0.05$, ##$p<0.01$, ###$p<0.001$. Significant differences of 10 vs A2: ^$p<0.05$, ^^$p<0.01$, ^^^$p<0.001$.

As shown in FIG. 8, the compound of Example 1 (10) shows a significant and sustained (most of the 8-hour test duration) increase of dopamine in the pre-frontal cortex, which is greater than with the deuterated compound of Example 1 (A2) from International Publication No. WO 2023/130117. 10 and A2 have the same number of deuterium substitutions, but in different positions.

The data indicates that the compound of Example 1 (10) may enhance perception of reward and cognition downstream of increased dopamine in the nucleus accumbens and pre-frontal cortex.

What is claimed:

1. A compound of Formula I:

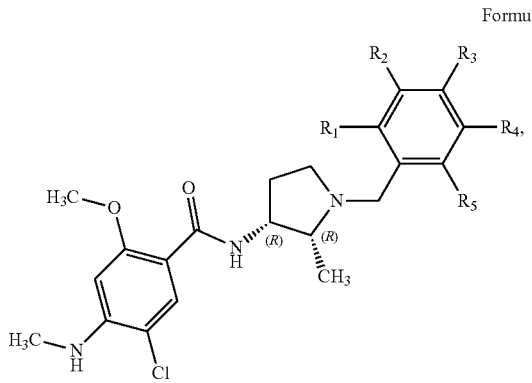

Formula I wherein:
$R_1$, $R_2$, $R_3$, $R_4$, and $R_5$ are independently selected from H and D; and
at least one of $R_1$, $R_2$, $R_3$, $R_4$, and $R_5$ is D;
in free or salt form.

2. The compound according to claim 1, wherein the compound is in free form.

3. A compound, wherein the compound is:

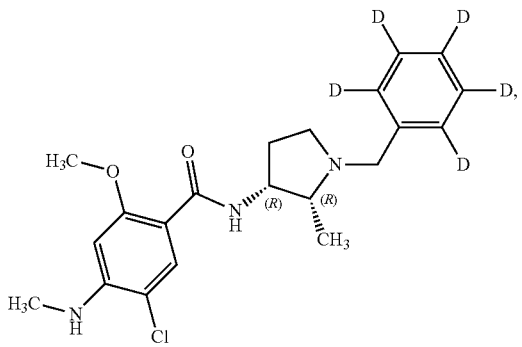

in free or pharmaceutically acceptable salt form.

4. The compound according to claim 1, wherein the compound, in free or pharmaceutically acceptable salt form, has greater than 90% incorporation of deuterium at one or more positions designated as deuterium.

5. A pharmaceutical composition, wherein the pharmaceutical composition comprises the compound according to claim 1, in free or pharmaceutically acceptable salt form, and a pharmaceutically acceptable carrier.

6. A method for treatment of an affective disorder or an anxiety disorder in a patient in need thereof, wherein the method comprises administering an effective amount of the compound according to claim 3, in free or pharmaceutically acceptable salt form, to the patient.

7. A method for treatment of depression, an anxiety disorder, a substance use disorder, psychosis, schizophrenia, schizoaffective disorder, post-traumatic stress disorder (PTSD), attention-deficit/hyperactivity disorder (ADHD), Tourette syndrome, anorexia nervosa, bulimia nervosa, binge-eating disorder, body dysmorphic disorder, obsessive compulsive disorder, addiction, bipolar disorder, or a migraine in a patient in need thereof, wherein the method comprises administering an effective amount of the compound according to claim 6, in free or pharmaceutically acceptable salt form, to the patient.

8. The method according to claim 7, wherein the anxiety disorder is panic disorder, social anxiety disorder, a phobia, or generalized anxiety disorder.

9. A method for treatment of anhedonia, depression associated with anhedonia, suicidal ideation, anxious depression, inflammatory depression, treatment-resistant depression, dysthymia, bipolar depression, psychotic depression, melancholic depression, or post-psychotic depression in a patient in need thereof, wherein the method comprises administering an effective amount of the compound according to claim 3, in free or pharmaceutically acceptable salt form, to the patient.

10. The method according to claim 9, wherein the method is for treatment of anxious depression.

11. The method according to claim 7, wherein the method is for treatment of melancholic depression.

12. A method for treatment of major depressive disorder in a patient in need thereof, wherein the method comprises administering an effective amount of the compound according to claim 3, in free or pharmaceutically acceptable salt form, to the patient.

13. The method according to claim 7, wherein the method is for treatment of post-traumatic stress disorder (PTSD).

14. The compound according to claim 3, wherein the compound is in free form.

15. The compound according to claim 3, wherein the compound, in free or pharmaceutically acceptable salt form, has greater than 90% incorporation of deuterium at the positions designated as deuterium.

16. The compound according to claim 14, wherein the compound, in free form, has greater than 90% incorporation of deuterium at the positions designated as deuterium.

17. A pharmaceutical composition, wherein the pharmaceutical composition comprises the compound according to claim 3, in free or pharmaceutically acceptable salt form, and a pharmaceutically acceptable carrier.

18. A pharmaceutical composition, wherein the pharmaceutical composition comprises the compound according to claim 14, in free form, and a pharmaceutically acceptable carrier.

19. A pharmaceutical composition, wherein the pharmaceutical composition comprises the compound according to claim 15, in free or pharmaceutically acceptable salt form, and a pharmaceutically acceptable carrier.

20. A pharmaceutical composition, wherein the pharmaceutical composition comprises the compound according to claim 16, in free form, and a pharmaceutically acceptable carrier.

21. The compound according to claim 3, wherein the compound, in free or pharmaceutically acceptable salt form, has greater than 96% incorporation of deuterium at the positions designated as deuterium.

22. The compound according to claim 14, wherein the compound, in free form, has greater than 96% incorporation of deuterium at the positions designated as deuterium.

23. A pharmaceutical composition, wherein the pharmaceutical composition comprises the compound according to claim 21, in free or pharmaceutically acceptable salt form, and a pharmaceutically acceptable carrier.

24. A pharmaceutical composition, wherein the pharmaceutical composition comprises the compound according to claim 22, in free form, and a pharmaceutically acceptable carrier.

25. A method for treatment of post-traumatic stress disorder (PTSD) in a patient in need thereof, wherein the method comprises administering an effective amount of the compound according to claim 21, in free or pharmaceutically acceptable salt form, to the patient.

26. A method for treatment of post-traumatic stress disorder (PTSD) in a patient in need thereof, wherein the method comprises administering an effective amount of the compound according to claim 22, in free form, to the patient.

\* \* \* \* \*